US012667244B2

(12) United States Patent
Sato

(10) Patent No.: US 12,667,244 B2
(45) Date of Patent: Jun. 30, 2026

(54) TREATMENT DEVICE, TREATMENT-TOOL OPERATING DEVICE, TREATMENT SYSTEM, AND TREATMENT-TOOL OPERATING METHOD

(71) Applicant: OLYMPUS CORPORATION, Tokyo (JP)

(72) Inventor: Hideyuki Sato, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 229 days.

(21) Appl. No.: 18/420,647

(22) Filed: Jan. 23, 2024

(65) Prior Publication Data

US 2024/0206710 A1     Jun. 27, 2024

Related U.S. Application Data

(63) Continuation of application No. PCT/JP2021/032407, filed on Sep. 3, 2021.

(51) Int. Cl.
*A61B 1/00* (2006.01)
*A61B 1/018* (2006.01)

(52) U.S. Cl.
CPC ...... *A61B 1/00133* (2013.01); *A61B 1/00135* (2013.01); *A61B 1/0014* (2013.01); *A61B 1/00154* (2013.01); *A61B 1/018* (2013.01)

(58) Field of Classification Search
CPC ............ A61B 1/00133; A61B 1/00135; A61B 1/0014; A61B 1/00154; A61B 1/018
See application file for complete search history.

(56) References Cited

U.S. PATENT DOCUMENTS 6,770,070 B1     8/2004  Balbierz
2005/0222495 A1  10/2005  Okada et al.
(Continued)

FOREIGN PATENT DOCUMENTS

EP     1582138 A2   10/2005
EP     2033590 A2    3/2009
(Continued)

OTHER PUBLICATIONS

"International Application Serial No. PCT/JP2021/032407, International Search Report dated Oct. 19, 2021", w/ English Translation, (Oct. 19, 2021).

(Continued)

*Primary Examiner* — Alazar Tilahun
(74) *Attorney, Agent, or Firm* — Schwegman Lundberg & Woessner, P.A.

(57) ABSTRACT

A treatment device includes a treatment tool and an outer tube connected to a long guide device and into which the tool is inserted, wherein the tube includes: a slack portion formed from a portion of the tube in a longitudinal direction of the tube, the slack portion being disposed in a slackened state; and a movable portion disposed on a proximal-end side of the slack portion, the movable portion being movable forward and backward in the longitudinal direction, and a slack amount of the slack portion changes as a result of the movable portion being moved forward and backward with respect to the tool, and, accordingly, a distal end of the tool disposed farther on a distal-end side than the slack portion is moved in the longitudinal direction.

16 Claims, 17 Drawing Sheets

(56)     References Cited

U.S. PATENT DOCUMENTS

| | | | |
|---|---|---|---|
| 2009/0062603 A1* | 3/2009 | Murakami | A61B 90/98 |
| | | | 600/104 |
| 2011/0184459 A1* | 7/2011 | Malkowski | A61B 17/29 |
| | | | 606/206 |
| 2013/0184528 A1 | 7/2013 | Onuki et al. | |
| 2015/0025315 A1 | 1/2015 | Nishina et al. | |
| 2016/0030124 A1 | 2/2016 | Kishi et al. | |

FOREIGN PATENT DOCUMENTS

| | | | |
|---|---|---|---|
| EP | 2596741 A1 | 5/2013 |
| EP | 2821001 A1 | 1/2015 |
| JP | 2003534037 A | 11/2003 |
| JP | 2005287963 A | 10/2005 |
| JP | 2009061250 A | 3/2009 |
| JP | 2009189703 A | 8/2009 |
| JP | 2013052258 A | 3/2013 |
| JP | 2016511013 A | 4/2016 |
| WO | WO-0170114 A1 | 9/2001 |
| WO | WO-2014017205 A1 | 1/2014 |
| WO | WO-2014129672 A1 | 8/2014 |

OTHER PUBLICATIONS

"International Application Serial No. PCT/JP2021/032407, Written Opinion dated Oct. 19, 2021", (Oct. 19, 2021), 3 pgs.

* cited by examiner

NATURAL ORIFICE

TREATMENT DEVICE, TREATMENT-TOOL OPERATING DEVICE, TREATMENT SYSTEM, AND TREATMENT-TOOL OPERATING METHOD

CROSS-REFERENCE TO RELATED APPLICATIONS

This is a continuation of International Application PCT/JP2021/032407 which is hereby incorporated by reference herein in its entirety.

TECHNICAL FIELD

The present invention relates to a treatment device, a treatment-tool operating device, a treatment system, and a treatment-tool operating method.

BACKGROUND ART

In the related art, there is a known treatment tool that is inserted into a body via a channel of an endoscope and that has a bending function (for example, see Patent Literatures 1 and 2). A distal-end portion of the treatment tool is bent as a result of an operating portion provided in a proximal-end portion of the treatment tool being operated, and a distal end of the treatment tool is moved forward and backward as a result of the proximal-end portion of the treatment tool being moved forward and backward. With such a combination of bending movements and forward-and-backward movements, it is possible to easily move the distal end of the treatment tool to a desired position.

CITATION LIST

Patent Literature

{PTL 1} Japanese Unexamined Patent Application, Publication No. 2009-189703
{PTL 2} Japanese Unexamined Patent Application, Publication No. 2013-52258

SUMMARY OF INVENTION

An aspect of the present invention is a treatment device with which a treatment tool is inserted into a body along a longitudinal direction of a long guide device, the treatment device including: a treatment tool; and an outer tube connected to the guide device and into which the treatment tool is inserted, wherein the outer tube includes: a slack portion formed from a portion of the outer tube in the longitudinal direction of the outer tube, the slack portion being disposed in a slackened state; and a movable portion disposed on a proximal-end side of the slack portion, the movable portion being movable forward and backward in the longitudinal direction of the outer tube with respect to the treatment tool in the outer tube, and a slack amount of the slack portion changes as a result of the movable portion being moved forward and backward with respect to the treatment tool, and, accordingly, a distal end of the treatment tool disposed farther on a distal-end side than the slack portion is moved in the longitudinal direction of the outer tube.

Another aspect of the present invention is a treatment-tool operating device with which a treatment tool inserted into a body along a longitudinal direction of a long guide device is operated, the treatment-tool operating device including: an outer tube connected to the guide device and into which the treatment tool is inserted, the outer tube including: a slack portion formed from a portion of the outer tube in a longitudinal direction of the outer tube, the slack portion being disposed in a slackened state; and a movable portion disposed on a proximal-end side of the slack portion, the movable portion being movable forward and backward in the longitudinal direction of the outer tube with respect to the treatment tool in the outer tube; a forward-and-backward operating portion connected to the movable portion of the outer tube and with which the movable portion is operated in the longitudinal direction of the outer tube; and joining portions configured to be joined with the treatment tool in a separable manner.

Another aspect of the present invention is a treatment system including: the above-described treatment device; and a long guide device to which the outer tube of the treatment device is connected.

Another aspect of the present invention is a treatment-tool operating method for moving a distal end of a treatment tool forward and backward, the method including: connecting an outer tube, into which the treatment tool is inserted, to a long guide device; forming a slack portion in the outer tube, the slack portion being formed from a portion of the outer tube in a longitudinal direction of the outer tube and disposed in a slackened state; and moving a movable portion of the outer tube disposed on a proximal-end side of the slack portion in the longitudinal direction of the outer tube with respect to the treatment tool in the outer tube.

BRIEF DESCRIPTION OF DRAWINGS

FIG. 3A is a longitudinal sectional view of the bending operating portion and the forward-and-backward operating portion in FIG. 2, showing a state in which the bending operating portion is in neutral.

FIG. 3B is a longitudinal sectional view of the bending operating portion and the forward-and-backward operating portion in FIG. 2, showing a state in which the bending operating portion is tilted.

FIG. 4A is a diagram for explaining forward and backward movements of the distal end of the treatment tool due to forward and backward movements of a proximal-end portion of an outer tube.

FIG. 4B is a diagram for explaining forward and backward movements of the distal end of the treatment tool due to forward and backward movements of the proximal-end portion of the outer tube, showing a state in which the proximal-end portion of the outer tube is moved backward from the position in FIG. 4A.

DESCRIPTION OF EMBODIMENTS

First Embodiment

A treatment device and a treatment system according to a first embodiment of the present invention will be described with reference to the drawings.

Figure 1A:
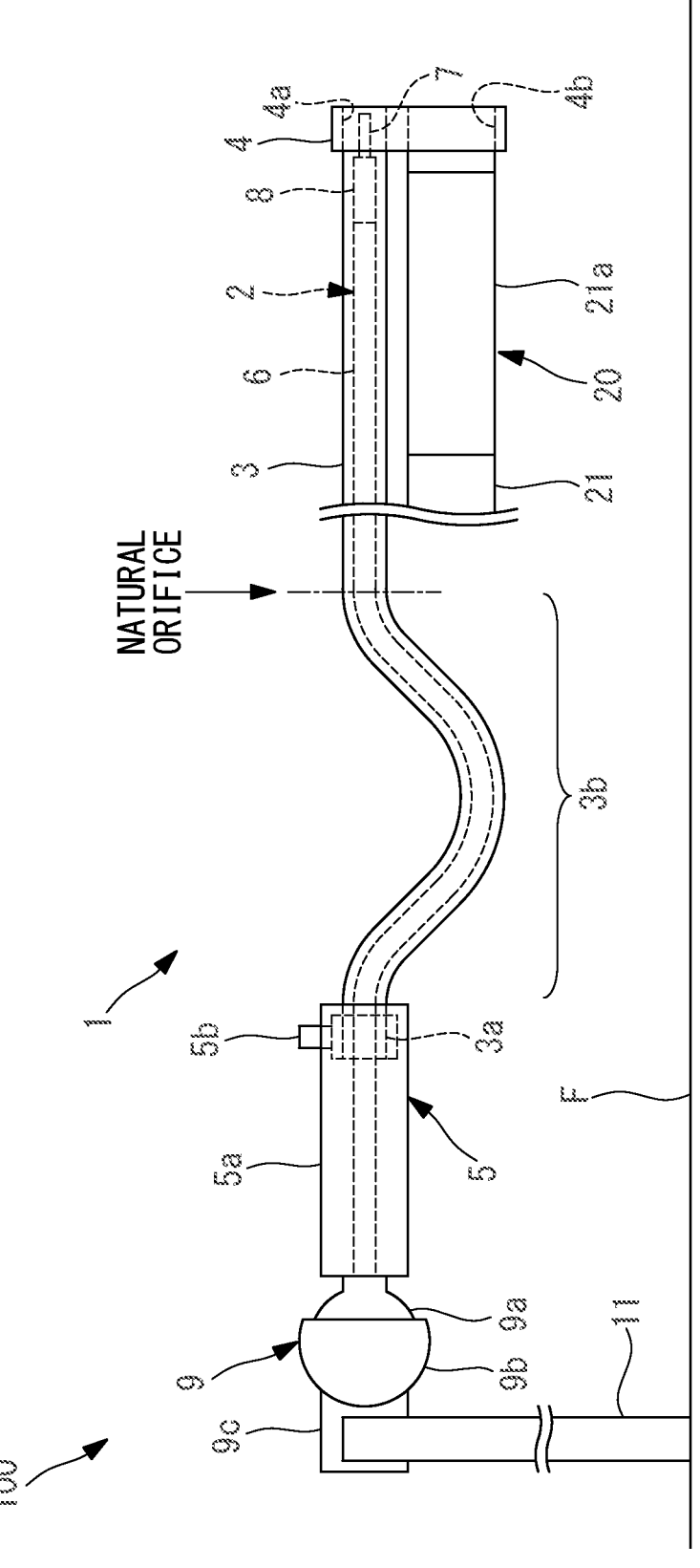
FIG. 1A is an overall configuration diagram of a treatment device and a treatment system according to a first embodiment of the present invention, showing a state in which a distal end of a treatment tool is moved backward.
Figure 1B:
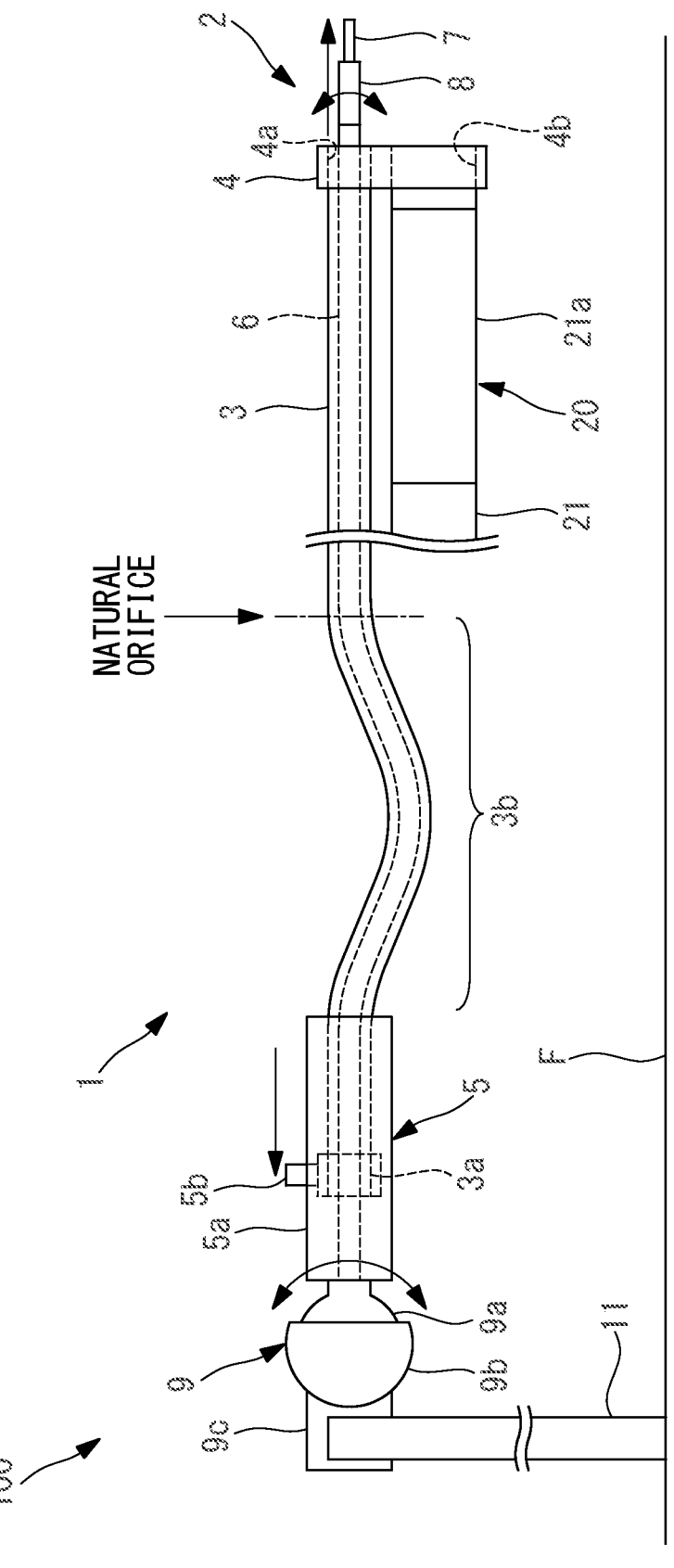
FIG. 1B is an overall configuration diagram of the treatment device and the treatment system according to the first embodiment of the present invention, showing a state in which the distal end of the treatment tool is moved forward.

As shown in FIGS. 1A and 1B, a treatment system 100 according to this embodiment is an endoscope system in which a treatment tool 2 is inserted into a body along a longitudinal direction of an endoscope 20. The treatment system 100 includes the endoscope (guide device) 20 and a treatment device 1 externally attached to the endoscope 20.

The endoscope 20 is a flexible endoscope, a laparoscope (rigid endoscope), or a medical manipulator that is inserted into a body of a patient from a natural orifice, such as the anus or the mouth. Hereinafter, a case in which the endoscope 20 is a flexible endoscope will be described. The endoscope 20 has a long insertion portion 21 possessing flexibility and an operating portion 22 that is connected to a proximal end of the insertion portion 21 and that is gripped by an operator (see FIG. 8). The insertion portion 21 has a bending portion 21a that is bendable in directions intersecting a longitudinal direction of the insertion portion 21 and the bending of the bending portion 21a is controlled by means of operations of the operating portion 22.

The treatment device 1 includes: the long treatment tool 2; an outer tube 3 into which the treatment tool 2 is inserted; a securing portion 4 that connects the outer tube 3 to the endoscope 20 in parallel thereto; and a forward-and-backward operating portion 5 that is operated by the operator and that causes the treatment tool 2 to be moved forward and backward.

Figure 3A:
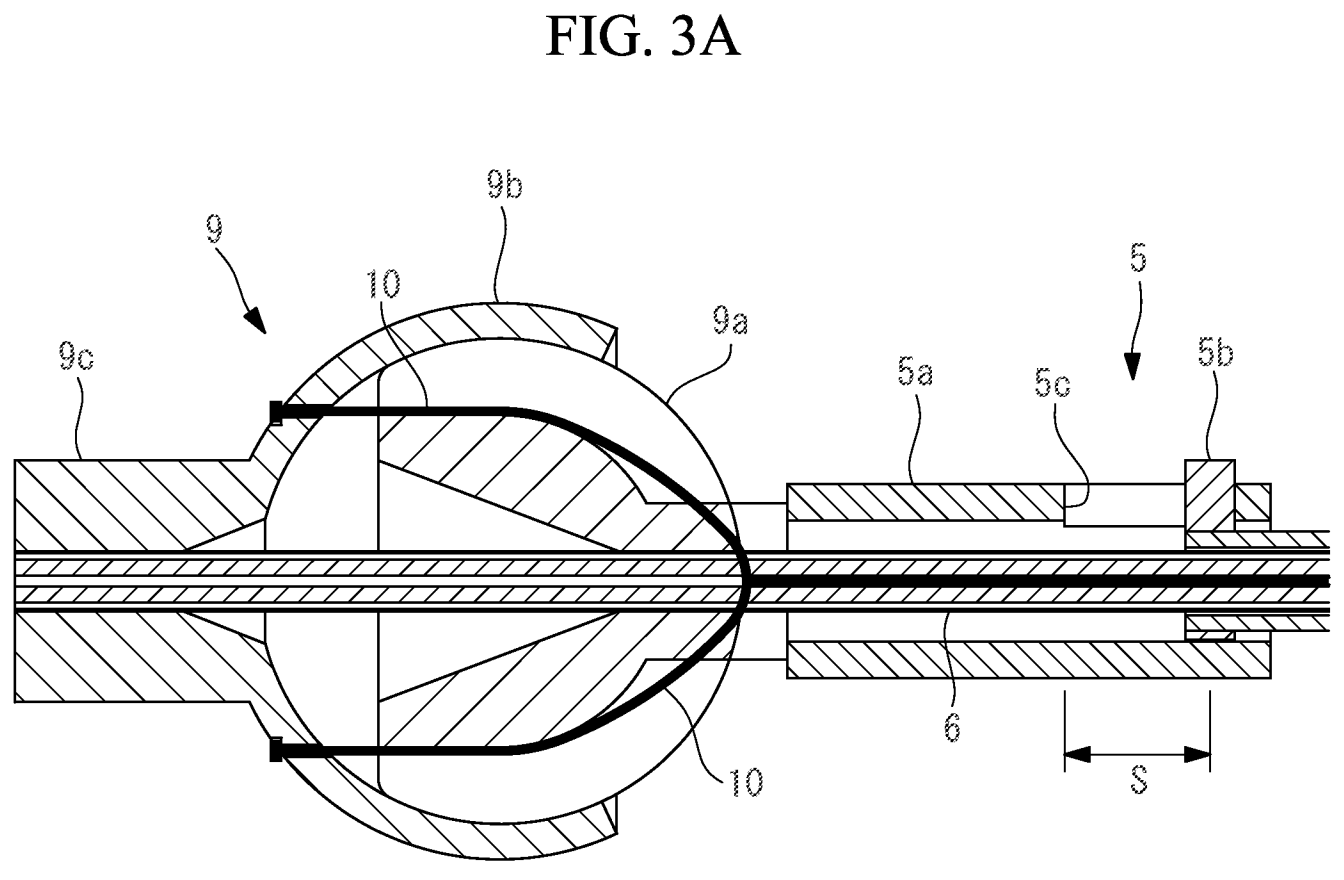
Figure 3B:
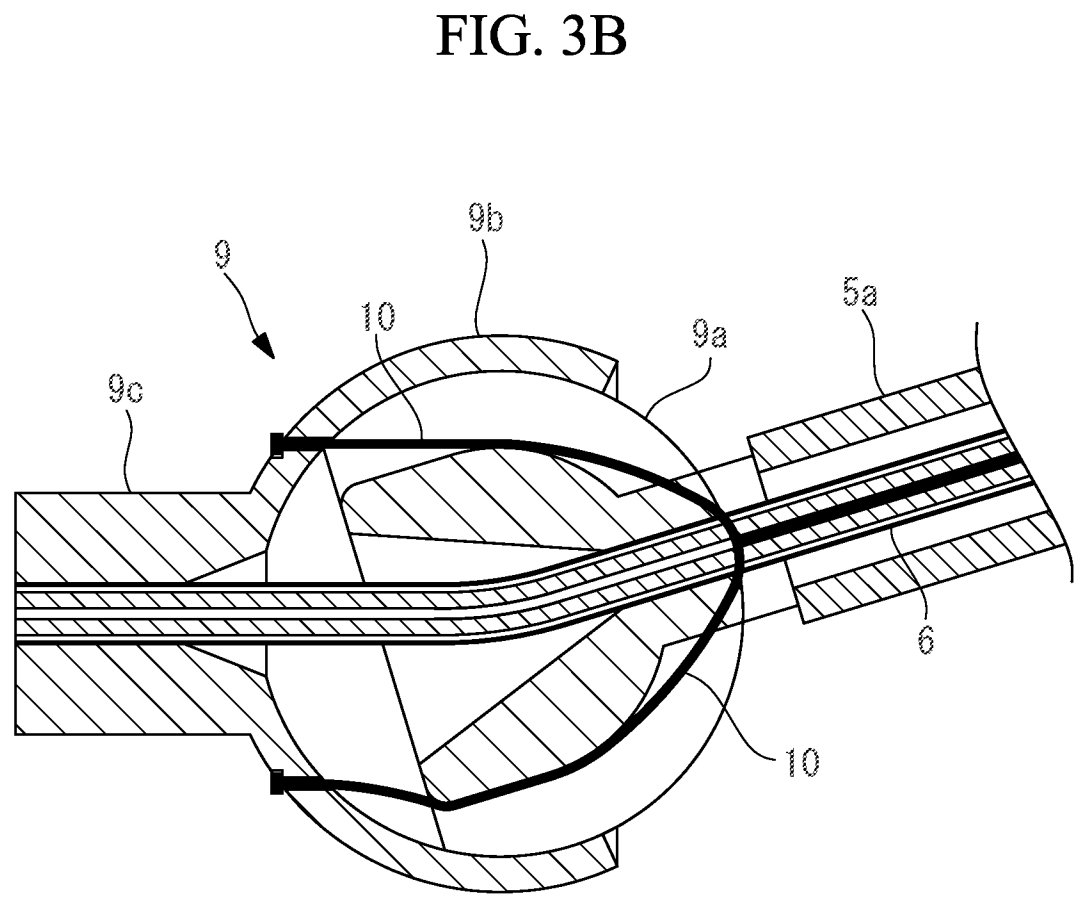

The treatment tool 2 includes: a long shaft 6 possessing flexibility; an effector 7 disposed on a distal-end side of the shaft 6; a bending portion 8 provided between a distal end of the shaft 6 and the effector 7; a bending operating portion 9 connected to a proximal-end portion of the shaft 6; and one or more bending wires 10 that connect the bending operating portion 9 and the bending portion 8 via the interior of the shaft 6 (see FIGS. 3A and 3B).

The shaft 6 consists of a tubular, long inner tube possessing flexibility. The one or more bending wires 10 are disposed in the interior of the shaft 6 along a longitudinal direction of the shaft 6, a distal end of each of the bending wires 10 is secured to the bending portion 8, and a proximal end of each of the bending wires 10 is secured to the bending operating portion 9.

The effector 7 is a portion that acts on living tissue and is, for example, a needle-like electrode.

The bending portion 8 connects the distal end of the shaft 6 and a proximal end of the effector 7 and is bendable in directions intersecting the longitudinal direction of the shaft 6. In this embodiment, the bending portion 8 is bendable in four directions, namely, up, down, left, and right, and four of the bending wires 10 are provided for respectively bending the bending portion 8 up, down, left, and right.

Figure 2:
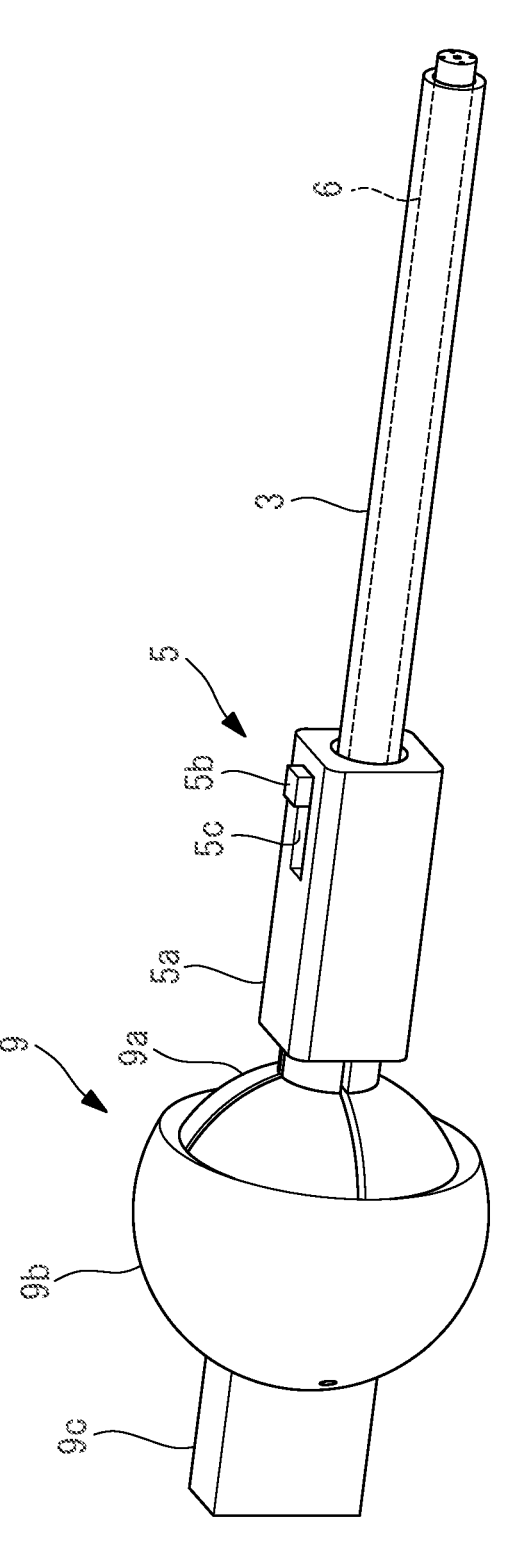
FIG. 2 is a perspective view showing external appearances of a bending operating portion and a forward-and-backward operating portion of the treatment device in FIGS. 1A and 1B.

As shown in FIGS. 2 to 3B, the bending operating portion 9 includes a ball 9a; a socket 9b that supports the ball 9a so as to be rotatable; and a securing portion 9c. FIGS. 3A and 3B are longitudinal sectional views of the operating portions 5 and 9 taken along the longitudinal axes of the outer tube 3 and the shaft 6.

The ball 9a has a partially spherical shape in which a portion thereof on a proximal-end side is cut out and the socket 9b has a partially spherical shell shape in which a portion thereof on a distal-end side is cut out. The socket 9b partially receives the ball 9a and supports the ball 9a so as to be rotatable in an arbitrary direction. As a result of the ball 9a being rotated in the socket 9b, the ball 9a and the forward-and-backward operating portion 5 are integrally tilted with respect to the socket 9b.

The shaft 6 extends through the forward-and-backward operating portion 5, and the ball 9a and is secured to the socket 9b. In the interior of the ball 9a, proximal-end portions of the four bending wires 10 are pulled out to the exterior of the shaft 6, and proximal ends of the four bending wires 10 are secured to the socket 9b at four positions about a prescribed center axis of the socket 9b with even spacings therebetween.

As shown in FIG. 3A, when the socket 9b, the ball 9a, and the forward-and-backward operating portion 5 are disposed on a straight line, tensile forces evenly act on the four bending wires 10 and the bending portion 8 extends straight along the longitudinal axis of the shaft 6. As shown in FIG. 3B, when the ball 9a and the forward-and-backward operating portion 5 are tilted with respect to the socket 9b, some of the four bending wires 10 are pulled and the bending portion 8 is consequently bent in a direction corresponding to the tilting direction. For example, when the ball 9a is tilted up, the bottom bending wire 10 is pulled and the bending portion 8 is consequently bent down.

The securing portion 9c is a portion for securing the position of the bending operating portion 9 with respect to a floor F. The securing portion 9c is a member that protrudes from an outer surface on a proximal-end side of the socket 9b and is secured to the socket 9b. As a result of the securing portion 9c being held by an arbitrary securing member 11, such as an arm or a stand, installed on the floor F, the bending operating portion 9 is held at a fixed position. The securing member 11 may be provided as part of the treatment system 100.

The outer tube 3 is a long, tubular member possessing flexibility over the entire length thereof and can be deformed by being flexibly bent. The outer tube 3 has an inner diameter that is greater than the outer diameters of the shaft 6, the effector 7, and the bending portion 8, and the outer tube 3 and the treatment tool 2 inside the outer tube 3 are movable relative to each other in the longitudinal direction of the outer tube 3. The outer tube 3 is shorter than the shaft 6 and the proximal-end portion of the shaft 6 and the bending portion 8 can respectively protrude from a proximal end and a distal end of the outer tube 3 at the same time. In addition, as will be described later, a portion in the longitudinal direction of the outer tube 3 disposed outside the body constitutes a slack portion 3b disposed in a slackened state.

The securing portion 4 is a member that secures a distal-end portion of the outer tube 3 to a distal-end portion of the insertion portion 21 positioned farther on the distal-end side than the bending portion 21a and that consequently connects and secures the outer tube 3 to the insertion portion 21 in parallel thereto. In the state in which the outer tube 3 is secured by the securing portion 4, the outer tube 3 extends toward the proximal end along the longitudinal direction of the insertion portion 21 from the distal end of the insertion portion 21.

In one configuration example, the securing portion 4 has two holes 4a and 4b that are disposed parallel to each other and that respectively extend through the securing portion 4. The distal-end portion of the outer tube 3 is inserted into the first hole 4a and is secured to an inner surface of the first hole 4a. As a result of inserting the distal-end portion of the insertion portion 21 into the second hole 4b, the securing portion 4 can be secured to an outer surface of the distal-end portion of the insertion portion 21 in a detachable manner. The securing portion 4 is secured to the distal-end portion of the insertion portion 21 due to friction between an inner surface of the second hole 4b and the outer surface of the insertion portion 21.

The forward-and-backward operating portion 5 is connected to a proximal-end portion (movable portion) 3a of the outer tube 3 and is disposed on the distal-end side of the bending operating portion 9. The forward-and-backward operating portion 5 has a cylindrical securing member 5a that is disposed in the longitudinal direction of the outer tube 3 and an operating member 5b that is secured to the proximal-end portion 3a and that is movable in the longitudinal direction of the outer tube 3 with respect to the securing member 5a.

A proximal end of the securing member 5a is secured to the ball 9a, and the shaft 6 of the treatment tool 2 extends through the interior of the securing member 5a and extends to the bending operating portion 9. The proximal-end portion 3a is inserted into the securing member 5a from the distal-end side of the securing member 5a and is movable in the securing member 5a in the longitudinal direction. A slot 5c that extends in the longitudinal direction is formed in the securing member 5a.

The operating member 5b protrudes outward from the securing member 5a via the slot 5c and is movable in the longitudinal direction in the slot 5c between a forward position and a backward position. By moving the operating member 5b forward and backward in the longitudinal direction, the operator can cause the proximal-end portion 3a to be moved forward and backward with respect to the shaft 6 and the bending operating portion 9.

Figure 4A:
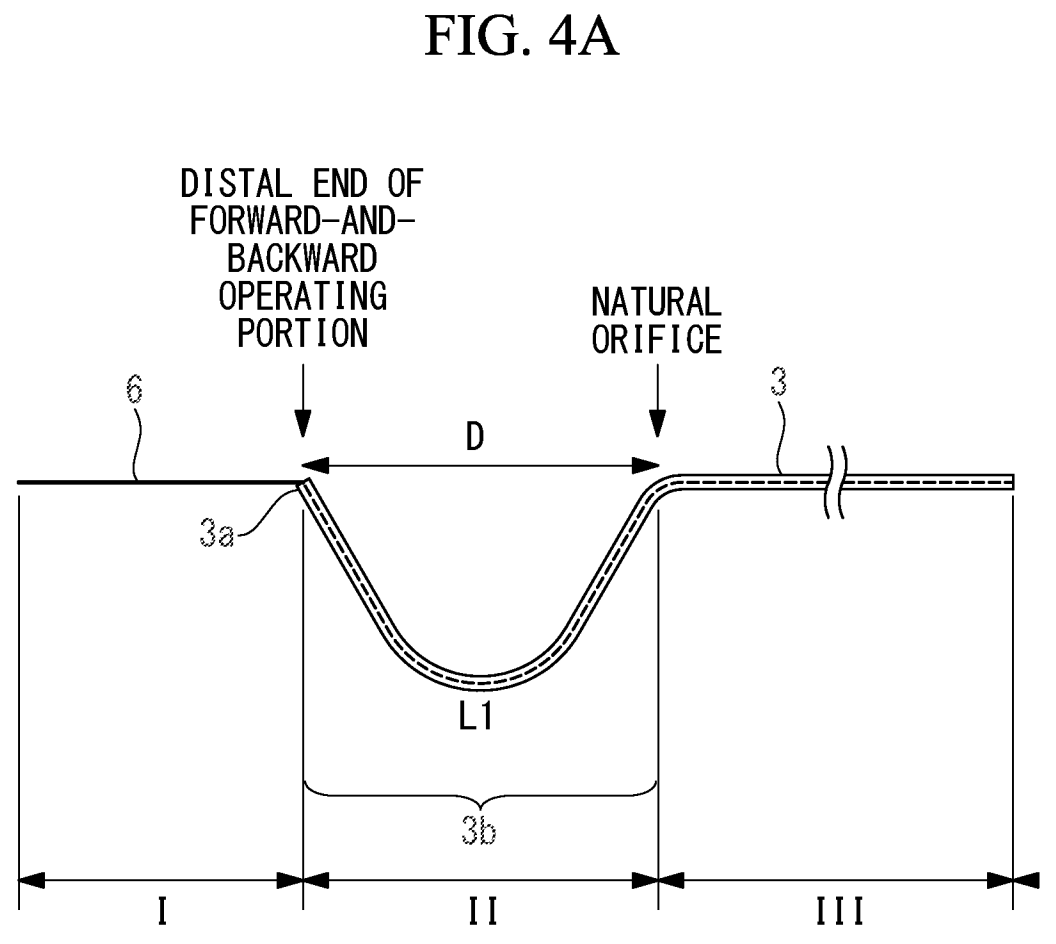
Figure 4B:
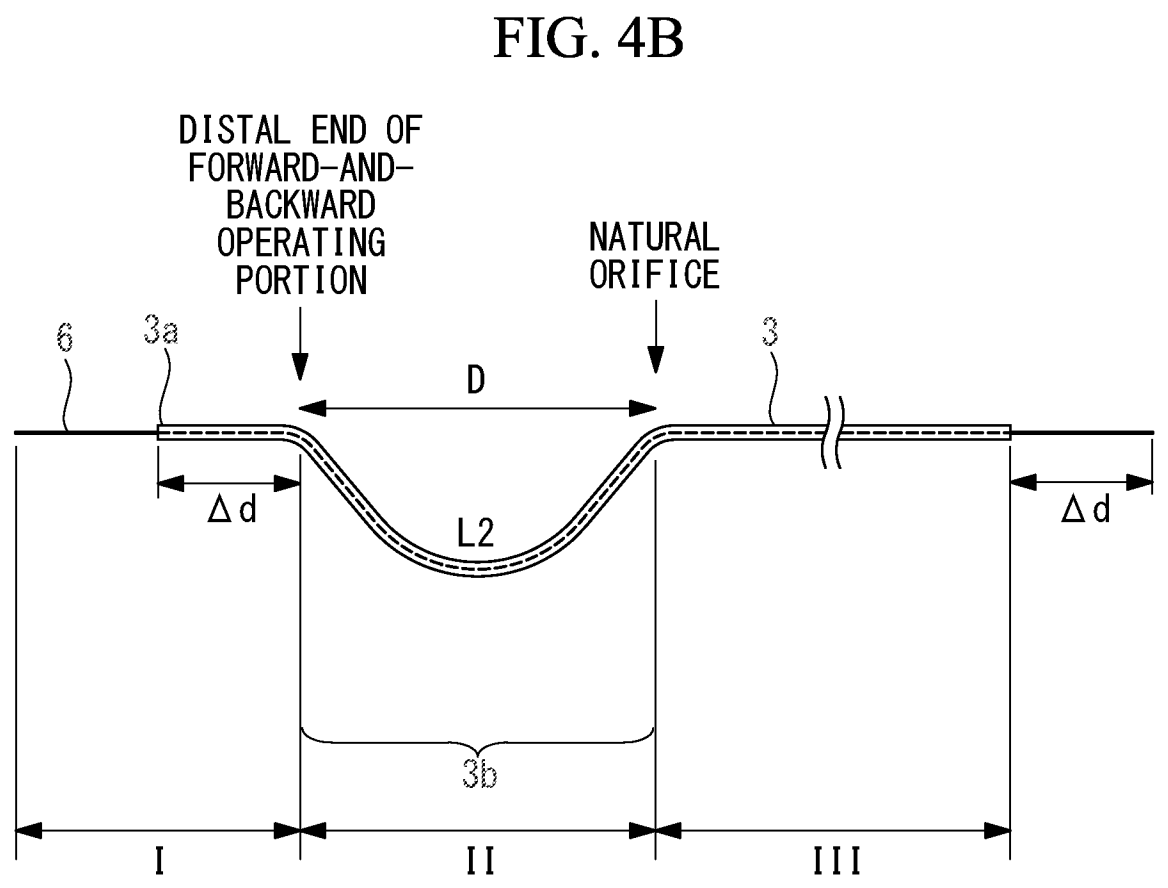

When the treatment device 1 is used, the outer tube 3 is inserted into the body of a patient from a natural orifice and the outer tube 3 is secured at the natural orifice. As shown in FIGS. 1A and 4A, as a result of installing the securing member 11 at an appropriate position with respect to the natural orifice, an extracorporeal portion of the outer tube 3, which is disposed between the natural orifice and the distal end of the forward-and-backward operating portion 5 (specifically, the distal end of the securing member 5a), forms the slack portion 3b disposed in a slackened state. As shown in FIGS. 1B and 4B, as a result of the proximal-end portion 3a being moved forward and backward due to the operation of the operating member 5b, a slack amount indicating a length L (L1, L2) of the slack portion 3b between the natural orifice and the distal end of the forward-and-backward operating portion 5 changes, and the distal end of the treatment tool 2 is consequently moved forward and backward.

Specifically, as shown in FIGS. 1A and 4A, when the operating member 5b is disposed at the forward position, the distal end of the treatment tool 2 is disposed at an initial position. The initial position is, for example, the same position as the distal end of the outer tube 3 in the longitudinal direction or a position that is slightly retracted from the distal end of the outer tube 3.

As shown in FIGS. 1B and 4B, as a result of the operating member 5b being moved back toward the backward position from the forward position, the slack amount of the slack portion 3b decreases, and the distal end of the treatment tool 2 is consequently moved forward from the initial position and protrudes from the distal end of the outer tube 3.

More specifically, in a section I, the length of the shaft 6 is constant regardless of the slack amount and, in a section III, the length of the shaft 6 is equal to the length of the outer tube 3 and constant regardless of the slack amount. In contrast, in a section II, the length of the shaft 6 is equal to the length of the outer tube 3 and changes together with the length of the outer tube 3 depending on the changes in the slack amount. Here, because the proximal-end position of the shaft 6 is fixed, the distal end of the shaft 6 is moved with respect to the outer tube 3 by an amount corresponding to the change amount in the length of the shaft 6 in the section II.

The section I is a section between the proximal end of the shaft 6 and the distal end of the forward-and-backward operating portion 5, the section II is a section between the forward-and-backward operating portion 5 and the natural orifice, and the section III is a section between the natural orifice and the distal end of the outer tube 3.

A movement amount $\Delta d$ of the distal end of the treatment tool 2 due to the operation of the operating member 5b is equal to an amount of change of the slack amount of the slack portion 3b, in other words, a movement amount $\Delta d$ of the operating member 5b, and is represented by the formula below:

$$\Delta d = |L1 - L2|,$$

where L1 is the length of the slack portion 3b before the operating member 5b is moved, and L2 is the length of the slack portion 3b after the operating member 5b is moved. Therefore, the slack amount of the slack portion 3b is adjusted to be equal to or greater than a desired movement amount (prescribed movement amount) of the distal end of the treatment tool 2.

A maximum movement amount of the distal end of the treatment tool 2 due to the operation of the operating member 5b is determined by a stroke (distance between the forward position and the backward position) S of the operating member 5b and is set, as appropriate, in accordance with the type, etc. of the treatment tool 2. For example, the stroke S is 30-40 mm. Slack of the slack portion 3b is adjusted so that the slack amount of the slack portion 3b when the operating member 5b is disposed at the forward position becomes equal to or greater than the maximum movement amount of the distal end of the treatment tool 2.

Next, an operating method for the treatment tool 2 using the treatment device 1 and the treatment system 100 will be described.

Figure 5:
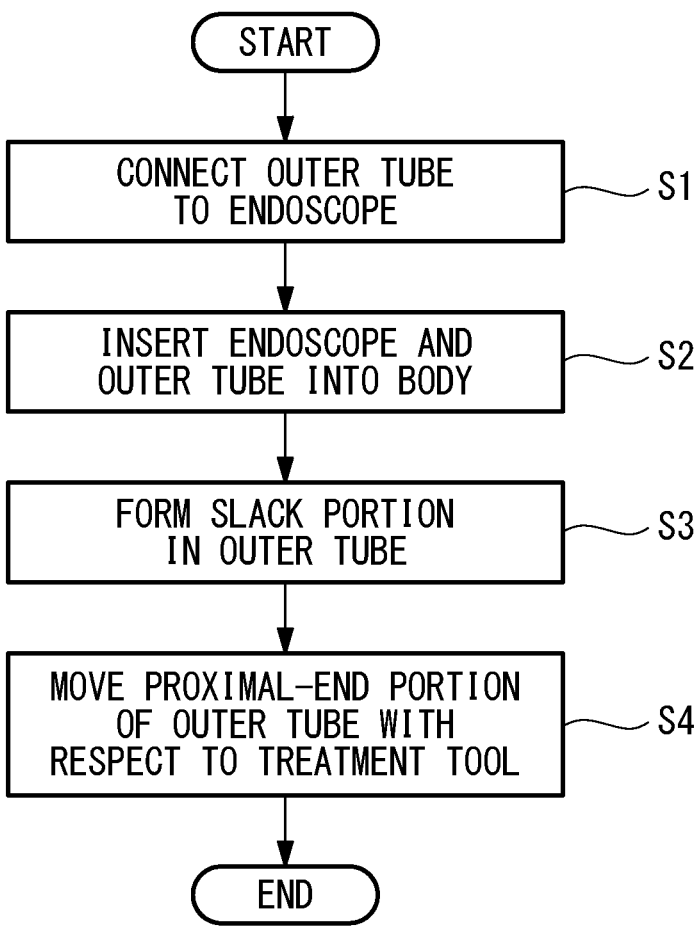
FIG. 5 is a flowchart showing a treatment-tool operating method according to the first embodiment of the present invention.

As shown in FIG. 5, a treatment-tool operating method according to this embodiment includes steps S1-S4.

First, a practitioner or an operator such as an assistant secures the distal-end portion of the outer tube 3 to the distal-end portion of the insertion portion 21 of the endoscope 20 by means of the securing portion 4 and consequently connects the outer tube 3, into which the treatment tool 2 is inserted, to the insertion portion 21 in parallel thereto (step S1).

Next, the operator inserts the insertion portion 21 into a body of a patient from a natural orifice, such as the anus, together with the outer tube 3 (step S2). Accordingly, the treatment tool 2 is inserted into the body along the longitudinal direction of the insertion portion 21.

Next, the operator forms the slack portion 3b in the extracorporeal portion of the outer tube 3 (step S3). Specifically, the securing member 11 holding the bending operating portion 9 is installed at a position at which the portion 3b of the outer tube 3 disposed between the natural orifice and the distal end of the forward-and-backward operating portion 5 is in a slackened state.

Next, by operating the operating portions 5 and 9, which are disposed on the proximal-end side of the slack portion 3b, the operator operates the distal end of the treatment tool 2 disposed in the body.

Specifically, when the operator wants to move the distal end of the treatment tool 2 forward, the operator causes, by moving the operating member 5b toward the backward position, the proximal-end portion 3a of the outer tube 3 to be moved backward (step S4). As a result of the proximal-end portion 3a being moved backward, the slack amount of the slack portion 3b decreases, and the distal end of the treatment tool 2 is consequently moved forward and protrudes from the distal end of the outer tube 3. The protruded distal end of the treatment tool 2 is disposed in the viewing field of the endoscope 20, and thus, observation can be performed by using an endoscope image.

In the state in which the bending portion 8 is protruded from the distal end of the insertion portion 21, the operator can cause, by tilting the ball 9a in any one direction together with the forward-and-backward operating portion 5, the bending portion 8 to be bent and the distal end of the treatment tool 2 to be moved in a radial direction of the treatment tool 2.

When the operator wants to move the distal end of the treatment tool 2 backward, the operator causes, by moving the operating member 5b toward the forward position, the proximal-end portion 3a of the outer tube 3 to be moved forward (step S4). As a result of the proximal-end portion 3a being moved forward, the slack amount of the slack portion 3b increases, and the distal end of the treatment tool 2 is consequently moved backward and pulled into the outer tube 3.

Here, in a case such as when one operator operates both of the treatment tool 2 and the endoscope 20 only with one hand, the operator sometimes temporarily releases his/her hand from the operating portions 5 and 9 while performing treatment and subsequently operates the operating portions 5 and 9 again. With this embodiment, due to the movement of the proximal-end portion 3a of the outer tube 3 with respect to the treatment tool 2, the distal end of the treatment tool 2, which is disposed farther on the distal-end side than the slack portion 3b, is moved forward and backward, and the position of the operating portions 5 and 9 as a whole is kept fixed. In other words, it is possible to move the distal end of the treatment tool 2 forward and backward without moving the operating portions 5 and 9, and the operating portions 5 and 9 are always disposed at the same positions; therefore, the operator can easily place his/her hand on the operating portions 5 and 9 again without having to check the positions of the operating portions 5 and 9.

Furthermore, in the case of a structure in which the distal end of the treatment tool 2 is moved forward and backward due to forward and backward movements of the whole operating portion on the proximal-end side of the treatment tool 2, the following problems could occur.

Specifically, because the operating portion and cords connected to the operating portion are moved, the operating portion and the cords may interfere with equipment, etc. in the surrounding area.

In addition, when the proximal-end portion of the treatment tool is unintentionally moved in the longitudinal direction as a result of the operator striking the operating portion due to carelessness, the distal end of the treatment tool is also unintentionally moved, and, for example, the distal end of the treatment tool may unintentionally protrude from the distal end of the endoscope.

With this embodiment, the operating portions 5 and 9 and the cords are kept in a stationary state while the treatment tool 2 is being operated; therefore, it is possible to prevent the operating portions 5 and 9 and the cords from interfering with an object in the surrounding area.

In addition, the slack amount of the slack portion 3b does not change due to the forward and backward movements of the operating portions 5 and 9 as a whole. Therefore, even if the operating portions 5 and 9 are moved due to the operator coming into contact with the operating portions 5 and 9 by mistake, because the operating member 5b does not move, the distal end of the treatment tool 2 is not moved forward or backward and is maintained at the same position. Accordingly, it is possible to prevent the distal end of the treatment tool 2 from being unintentionally moved forward or backward.

In addition, it suffices that the length of the rigid forward-and-backward operating portion 5 be slightly longer than the stroke S of the operating member 5b. Therefore, it is possible to realize a compact forward-and-backward operating portion 5.

In addition, because the position and the posture of the socket 9b supporting the ball 9a are fixed by the securing member 11, the correspondence relationship between the tilting direction of the ball 9a and the bending direction of the bending portion 8 is kept constant. Therefore, the operator can intuitively operate the bending portion 8 by means of the bending operating portion 9.

In this embodiment, the securing portion 4 secures the distal-end portion of the outer tube 3 to the distal-end portion of the insertion portion 21 of the endoscope 20; alternatively, however, the outer tube 3 may be secured to other portion of the insertion portion 21.

For example, the securing portion 4 may secure the outer tube 3 on the proximal-end side of the bending portion 21a. With this configuration, it is possible to bend the bending portion 21*a* of the endoscope 20 while maintaining the position of the distal end of the treatment tool 2.

In this embodiment, the treatment tool 2 has the effector 7 at the distal end thereof; however, the treatment tool 2 need not have the effector 7. For example, the treatment tool 2 may be equipment from which a fluid, such as water, a drug, or a gas, is supplied or discharged via the interior of an inner tube constituting the shaft 6.

Figure 6:
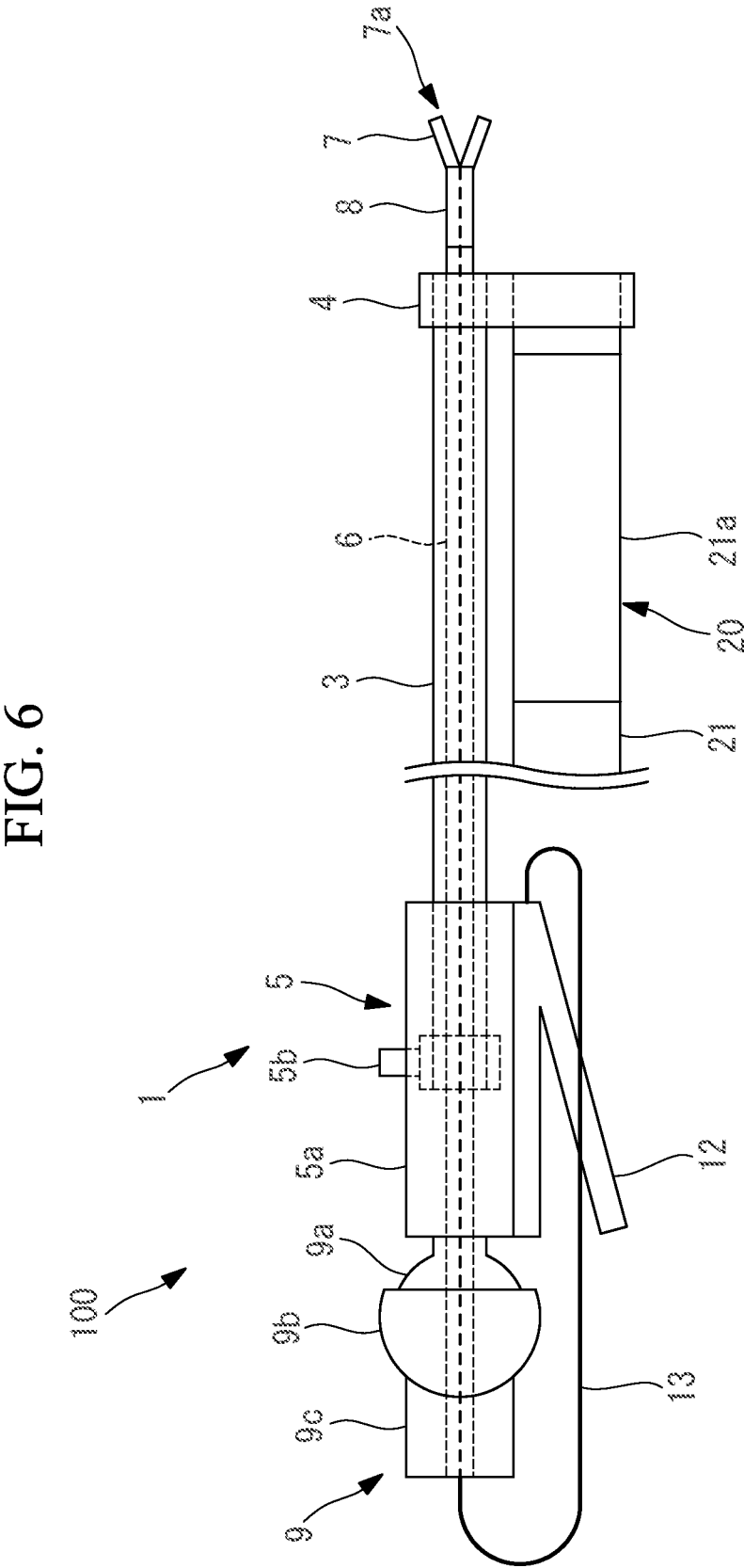
FIG. 6 is an overall configuration diagram of a modification of the treatment device and the treatment system in FIGS. 1A and 1B.

In this embodiment, in the case in which the effector 7 has a movable portion 7*a* that is mechanically moved, as shown in FIG. 6, the treatment tool 2 may additionally include an effector operating portion 12 for operating the movable portion 7*a*. For example, the movable portion 7*a* may be a plurality of gripping members that can be opened and closed with respect to each other.

In this case, the treatment tool 2 additionally includes a driving wire 13 that extends from the effector operating portion 12, passes through the interior of the shaft 6, and reaches the effector 7 and that connects the effector operating portion 12 and the movable portion 7*a*. As a result of the operator operating the effector operating portion 12 (for example, as a result of a handle of the effector operating portion 12 being swung), the driving wire 13 is pulled or fed, and the movable portion 7*a* is consequently moved.

It is preferable that the effector operating portion 12 be attached to the forward-and-backward operating portion 5. With this configuration, the operator can perform the forward-and-backward operation of the distal end of the treatment tool 2, the bending operation of the bending portion 8, and the operation of the movable portion 7*a* by using only one hand.

In this embodiment, the positions of the operating portions 5 and 9 are fixed by the securing member 11 with respect to the floor F; alternatively, however, the operating portions 5 and 9 may be fixed with respect to other object.

In one modification, the operating portions 5 and 9 may be secured by one hand of a practitioner or an operator such as an assistant who grips the bending operating portion 9. In this case, the forward-and-backward operating portion 5 is operated by the opposite hand (for example, right hand) from the one hand (for example, left hand) gripping the bending operating portion 9.

In another modification, the operating portions 5 and 9 may be secured to the insertion portion 21 or the operating portion 22 of the endoscope 20.

The operating portions 5 and 9 secured to the insertion portion 21 are suitable for operating both the treatment tool 2 and the insertion portion 21. As a result of the operating portions 5 and 9 being disposed at the insertion portion 21, it is possible to easily perform, with one hand, both of the operations for moving the insertion portion 21 forward and backward and twisting the portion and the operation of the treatment tool 2.

The operating portions 5 and 9 secured to the operating portion 22 are suitable for operating both the treatment tool 2 and another treatment tool inserted into a channel 23 (see FIG. 8) of the endoscope 20. The other treatment tool is inserted into the channel 23 from an entrance 23*a* provided in the operating portion 22. As a result of the bending operating portion 9 being disposed at the operating portion 22, it is possible to easily operate, with one hand, both the treatment tool 2 and the other treatment tool.

Second Embodiment

Next, a treatment device and a treatment system according to a second embodiment of the present invention will be described with reference to the drawings.

The treatment system according to this embodiment differs from that of the first embodiment in that the forward-and-backward operating portion 5 additionally includes a reversing mechanism 14. In this embodiment, features that are different from the first embodiment will be described and configurations that are the same as the first embodiment will be given the same reference signs and the descriptions thereof will be omitted.

The treatment system according to this embodiment is an endoscope system including the endoscope 20 and the treatment device 1.

The treatment device 1 includes the treatment tool 2, the outer tube 3, the securing portion 4, and a forward-and-backward operating portion 51 that is connected to the proximal-end portion 3*a* of the outer tube 3.

Figure 7A:
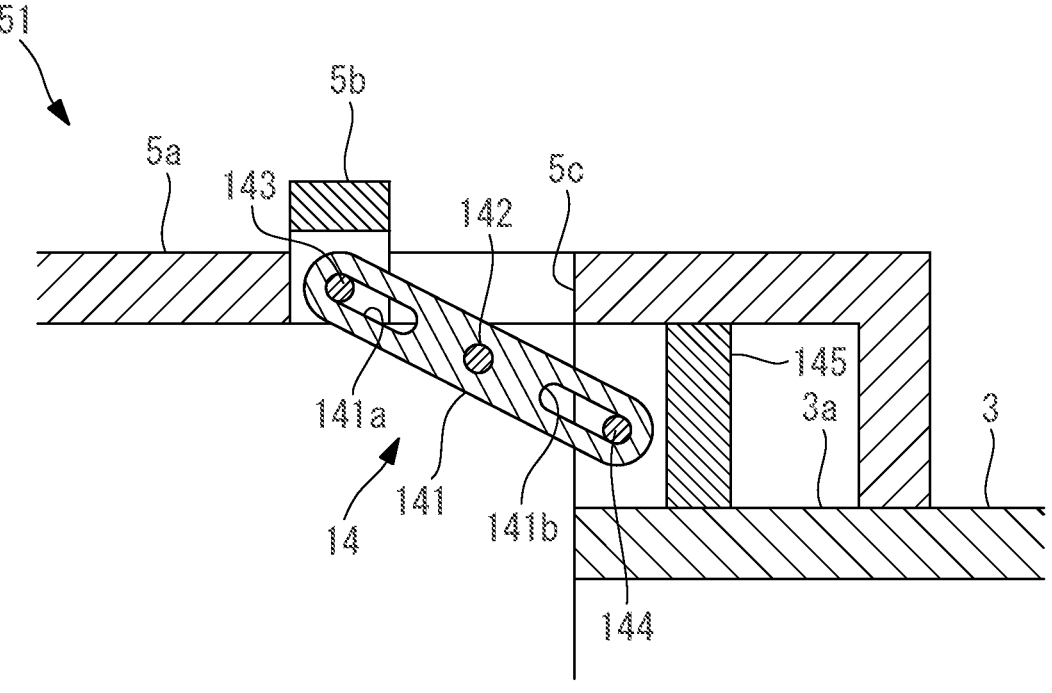
FIG. 7A is a partial sectional view of a configuration example of a forward-and-backward operating portion of a treatment device according to a second embodiment of the present invention.
Figure 7B:
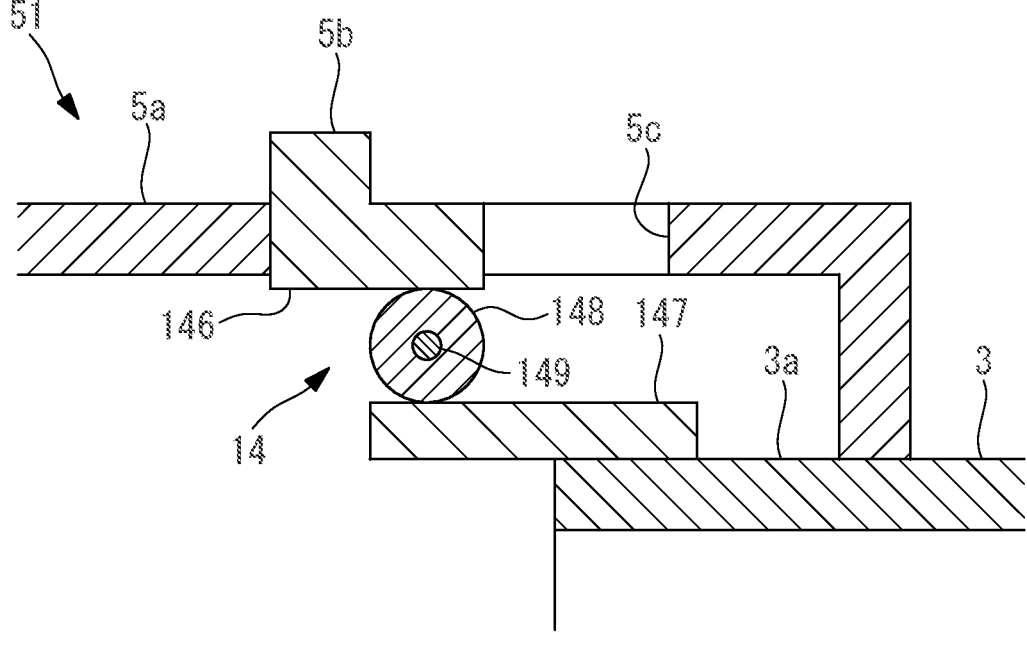
FIG. 7B is a partial sectional view of another configuration example of the forward-and-backward operating portion of the treatment device according to the second embodiment of the present invention.

As shown in FIGS. 7A and 7B, the forward-and-backward operating portion 51 includes the securing member 5*a*, the operating member 5*b*, and the reversing mechanism 14 that moves the proximal-end portion 3*a* in a direction opposite from the moving direction of the operating member 5*b*.

In this embodiment, the operating member 5*b* is connected to the proximal-end portion 3*a* by the reversing mechanism 14.

The reversing mechanism 14 converts the movement of the operating member 5*b* into a movement in the opposite direction and transmits the movement in the opposite direction to the proximal-end portion 3*a*. Accordingly, the reversing mechanism 14 causes the proximal-end portion 3*a* to be moved backward when the operating member 5*b* is moved forward and causes the proximal-end portion 3*a* to be moved forward when the operating member 5*b* is moved backward.

FIGS. 7A and 7B show configuration examples of the reversing mechanism 14.

The reversing mechanism 14 in FIG. 7A consists of a linkage mechanism. Specifically, this reversing mechanism 14 has a linkage 141 supported by the securing member 5*a* so as to be rotatable about a rotation shaft 142. One end of the linkage 141 is linked to the operating member 5*b* so as to be rotatable about a support shaft 143, and the other end of the linkage 141 is linked to a movable member 145 secured to the proximal-end portion 3*a* so as to be rotatable about a support shaft 144. The rotation shaft 142 is disposed at a center of the linkage 141 in the longitudinal direction, and the shafts 142, 143, and 144 extend in a direction orthogonal to both an arraying direction of the operating member 5*b* and the outer tube 3 (top-to-bottom vertical direction in FIG. 7A) and the moving direction of the operating member 5*b* (lateral direction in FIG. 7A). In order to keep the distance between the operating member 5*b* and the outer tube 3 in the arraying direction constant, the support shafts 143 and 144 are movable in long holes 141*a* and 141*b* formed at the two end portions of the linkage 141.

The reversing mechanism 14 in FIG. 7B consists of a rack and pinion. Specifically, this reversing mechanism 14 includes a first rack 146 secured to the operating member 5*b*, a second rack 147 secured to the proximal-end portion 3*a* of the outer tube 3, and a pinion 148 that is supported by the securing member 5*a* so as to be rotatable about a rotation shaft 149 and that engages with both the racks 146 and 147. The rotation shaft 149 extends in a direction orthogonal to both the arraying direction of the operating member 5*b* and the outer tube 3 (top-to-bottom vertical direction in FIG. 7B) and the moving direction of the operating member 5*b* (lateral direction in FIG. 7B).

With this embodiment, as a result of the reversing mechanism 14 being provided in the forward-and-backward operating portion 51, the moving direction of the operating member 5*b* is aligned with the moving direction of the distal end of the treatment tool 2. In other words, the forward movement of the operating member 5*b* causes the distal end of the treatment tool 2 to be moved forward, and the backward movement of the operating member 5*b* causes the distal end of the treatment tool 2 to be moved backward. Therefore, the operator can more intuitively operate the distal end of the treatment tool 2.

Other operational effects of this embodiment are the same as those of the first embodiment; therefore, the descriptions thereof will be omitted.

It is possible to apply the modifications described in the first embodiment to this embodiment.

Specifically, the securing portion 4 may secure the outer tube 3 to a portion of the endoscope 20 other than the distal-end portion of the insertion portion 21.

The treatment tool 2 may not have the effector 7.

In the case in which the effector 7 has the movable portion 7*a*, the treatment tool 2 may additionally include the effector operating portion 12, and the effector operating portion 12 may be attached to the forward-and-backward operating portion 51.

The bending operating portion 9 may be secured with respect to an object other than the floor F, such as the hand of the operator, the insertion portion 21, or the operating portion 22.

Third Embodiment

Next, a treatment device and a treatment system according to a third embodiment of the present invention will be described with reference to the drawings.

Figure 8:
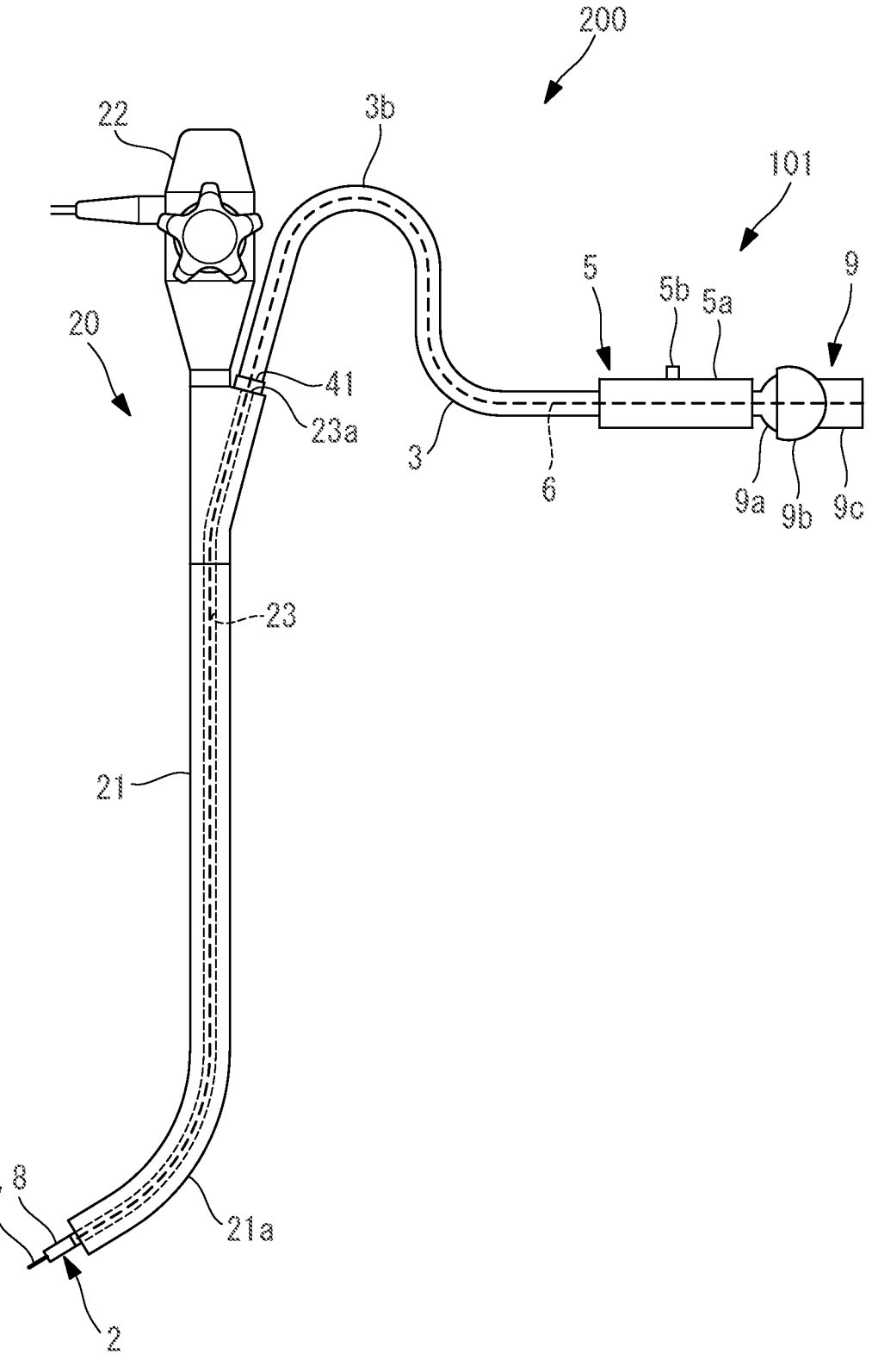
FIG. 8 is an overall configuration diagram of a treatment device and a treatment system according to a third embodiment of the present invention.

As shown in FIG. 8, a treatment system 200 according to this embodiment differs from that of the first embodiment in that the outer tube 3 is connected to the channel 23 of the endoscope 20 in series. In this embodiment, features that are different from the first embodiment will be described and configurations that are the same as the first embodiment will be given the same reference signs and the descriptions thereof will be omitted.

The treatment system 200 is an endoscope system including the endoscope 20 and a treatment device 101.

The endoscope 20 has the channel 23 that extends through the insertion portion 21 in the longitudinal direction of the insertion portion 21 and into which the treatment tool 2 is inserted. The channel 23 extends from the entrance 23*a* provided in the operating portion 22 to an exit provided in a distal-end surface of the insertion portion 21.

The treatment device 101 includes the treatment tool 2, the outer tube 3, a securing portion 41 that connects the outer tube 3 to the channel 23 of the endoscope 20 in series, and the forward-and-backward operating portion 5.

The securing portion 41 is, for example, a cylindrical member that is secured at the distal end of the outer tube 3 and that can be press fitted into the entrance 23*a*. The shaft 6 passes through the interiors of the forward-and-backward operating portion 5 and the outer tube 3 and extends from the distal end of the securing portion 41.

As a result of inserting the treatment tool 2 into the channel 23 from the effector 7 side and press fitting the securing portion 41 into the entrance 23*a*, the distal end of the outer tube 3 is connected and secured to the entrance 23*a* at the proximal end of the channel 23, and thus, the treatment device 101 can be mounted to the endoscope 20. The outer tube 3 is sufficiently shorter than the shaft 6 and has a sufficient length for the bending portion 8 of the treatment tool 2 to protrude from the distal end of the insertion portion

21 and the proximal-end portion of the shaft 6 to protrude from the proximal end of the outer tube 3.

In this embodiment, the entire outer tube 3 is disposed outside the body and the slack portion 3*b* is formed from a portion between the proximal end of the securing portion 41 and the distal end of the forward-and-backward operating portion 5.

Next, an operating method for the treatment tool 2 using the treatment device 101 and the treatment system 200 will be described.

First, the operator inserts the insertion portion 21 into a body of a patient from a natural orifice.

Next, the operator inserts the treatment tool 2 into the channel 23 from the distal-end side and secures the distal-end portion of the outer tube 3 to the entrance 23*a* of the channel 23 by the securing portion 41, and thereby connecting the outer tube 3 to the insertion portion 21 in series. Accordingly, the treatment tool 2 is inserted into the body along the longitudinal direction of the insertion portion 21.

Next, the operator forms the slack portion 3*b* in the outer tube 3. Specifically, the securing member 11 (not shown) holding the bending operating portion 9 is installed at a position at which the portion 3*b* of the outer tube 3 disposed between the proximal end of the securing portion 41 and the distal end of the forward-and-backward operating portion 5 is placed in the slackened state.

Next, the operator can operate the distal end of the treatment tool 2 disposed inside the body by operating the operating portions 5 and 9 disposed on the proximal-end side of the slack portion 3*b*.

Other operational effects of this embodiment are the same as those of the first embodiment; therefore, the descriptions thereof will be omitted.

In this embodiment, the treatment system 200 includes the endoscope 20 as a guide device; alternatively, however, the treatment system 200 may include other guide device for introducing the treatment tool 2 into a body and the outer tube 3 may be connected to the other guide device in series.

Figure 9:
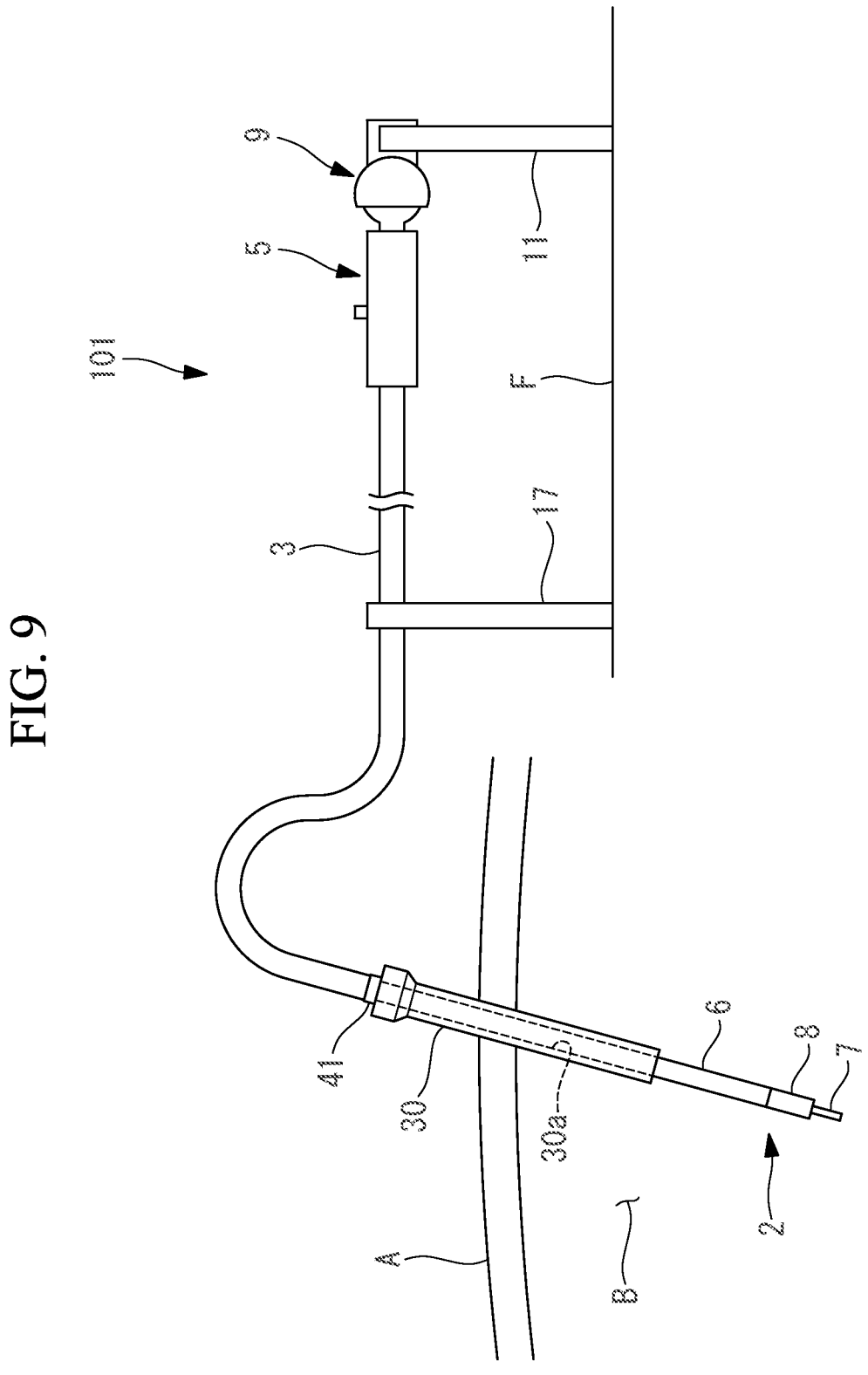
FIG. 9 is an overall configuration diagram of a modification of the treatment device and the treatment system in FIG. 8.

FIG. 9 shows an example in which the treatment device 101 is applied to a trocar (guide device) 30 used in a laparoscopic surgery. The trocar 30 is a long cylindrical member, has a channel 30*a* that extends through the trocar 30 in the longitudinal direction and into which the treatment tool 2 is inserted, and is inserted into an abdominal cavity B by passing through a body wall A. The securing portion 41 connects the distal end of the outer tube 3 to the proximal end of the trocar 30 to be secured thereto. In this modification, an intermediate position in the longitudinal direction of the outer tube 3 is secured with respect to the floor F by another securing member 17 and the slack portion 3*b* is provided at an arbitrary position between the distal end of the forward-and-backward operating portion 5 and the securing member 17.

It is possible to apply the modifications described in the first embodiment to this embodiment.

In other words, the treatment tool 2 may not have the effector 7.

In the case in which the effector 7 has the movable portion 7*a*, the treatment tool 2 may additionally include the effector operating portion 12 and the effector operating portion 12 may be attached to the forward-and-backward operating portion 5.

The bending operating portion 9 may be secured with respect to an object other than the floor F, such as the hand of the operator.

Fourth Embodiment

Next, a treatment device and a treatment system according to a fourth embodiment of the present invention will be described with reference to the drawings.

Figure 10:
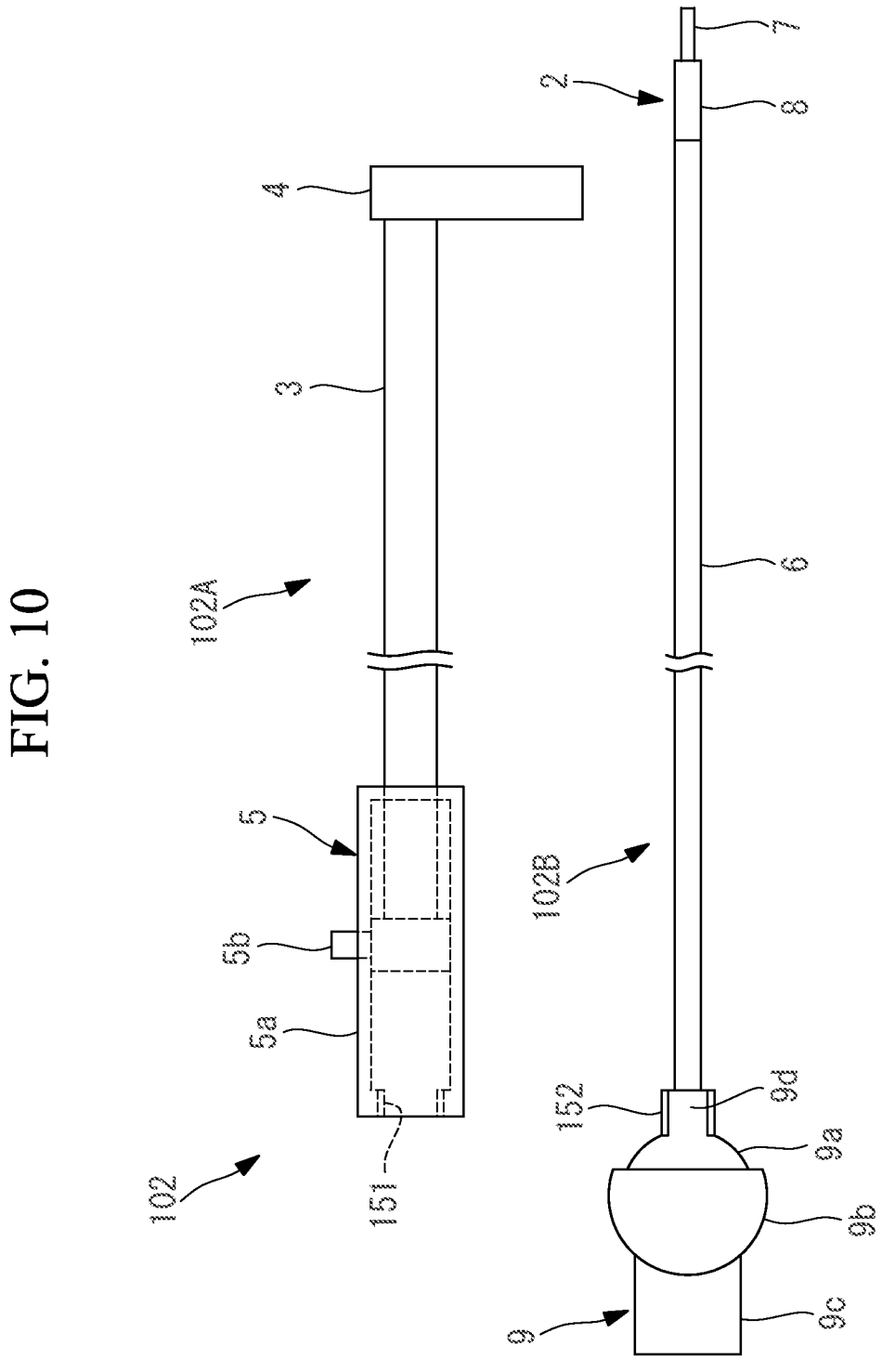
FIG. 10 is an overall configuration diagram of a treatment device according to a fourth embodiment of the present invention.

As shown in FIG. 10, an endoscope system according to this embodiment differs from that of the first embodiment in that a treatment device 102 includes two devices 102A and 102B that are separated from each other. In this embodiment, features that are different from the first embodiment will be described and configurations that are the same as the first embodiment will be given the same reference signs and the descriptions thereof will be omitted.

The treatment system according to this embodiment is an endoscope system including the endoscope 20 (not shown) and the treatment device 102 that is externally attached to the endoscope 20.

The treatment device 102 includes the first device 102A, the second device 102B, and joining portions 151 and 152 that join the first device 102A and the second device 102B in a separable manner. The first device 102A has the outer tube 3, the securing portion 4, and the forward-and-backward operating portion 5. The second device 102B has the treatment tool 2.

The first joining portion 151 is provided in the forward-and-backward operating portion 5, the second joining portion 152 is provided in the bending operating portion 9, and the joining portions 151 and 152 can be joined with each other and separated from each other. As a result of inserting the treatment tool 2 into the forward-and-backward operating portion 5 and the outer tube 3 from the proximal-end side of the first device 102A and joining the second joining portion 152 with the first joining portion 151, the forward-and-backward operating portion 5 and the bending operating portion 9 are locked so as not to be moved relative to each other in the longitudinal direction, and thus, the two devices 102A and 102B are integrally assembled. In the integrally assembled state, the distal end of the treatment tool 2 is movable forward and backward due to the forward and backward movements of the operating member 5b of the forward-and-backward operating portion 5.

In one configuration example, the first joining portion 151 is an annular member having a female thread on an inner surface thereof and is provided on an inner surface of a hole that is provided in a proximal-end surface of the securing member 5a and into which a shaft portion 9d is inserted. The second joining portion 152 is an annular member having, on an outer surface thereof, a male thread to be fastened to the female thread of the first joining portion 151 and is provided on an outer surface of the shaft portion 9d that protrudes from the distal-end surface of the ball 9a and that is inserted into the hole of the securing member 5a.

Figure 11A:
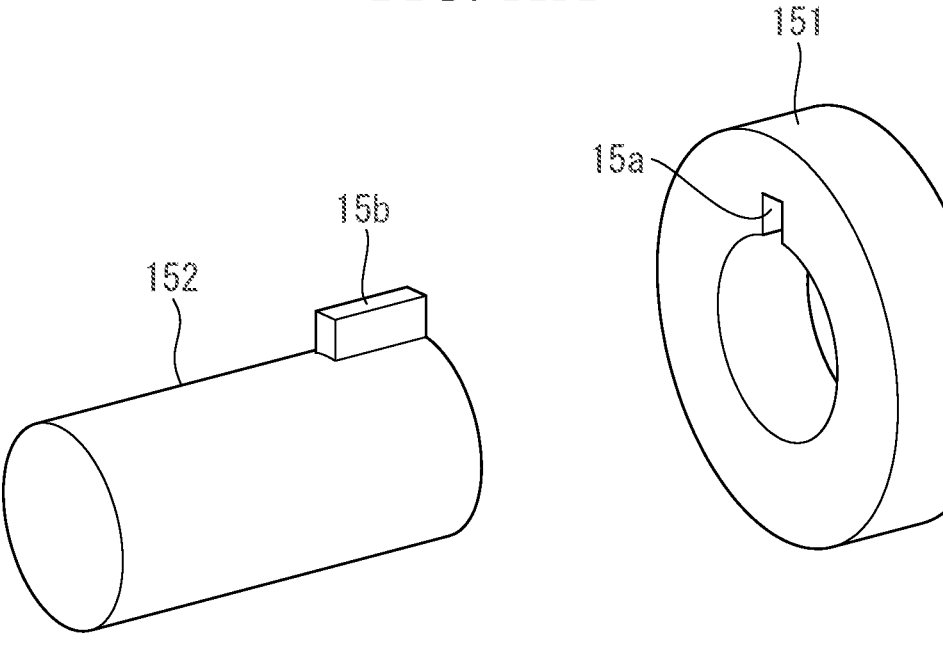
FIG. 11A is a perspective view of another configuration example of joining portions that join a first device and a second device.
Figure 11B:
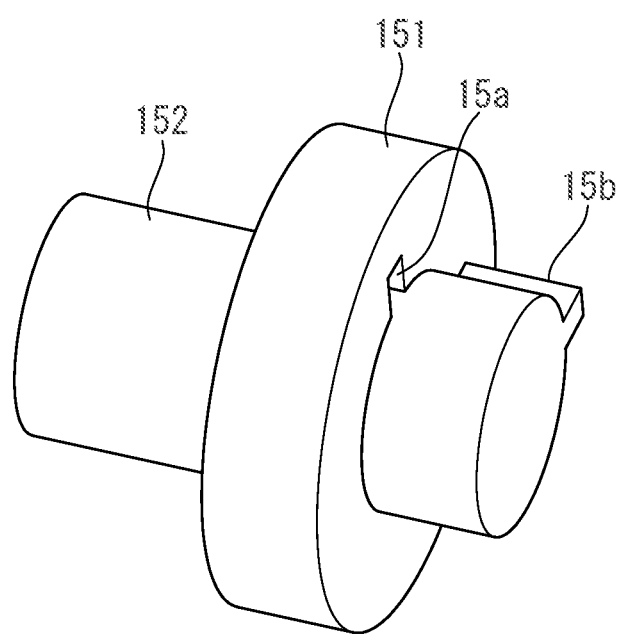
FIG. 11B is a perspective view of the joining portions in FIG. 11A in a locked state.

FIGS. 11A and 11B show another configuration example of the joining portions 151 and 152. In this configuration example, the first joining portion 151 is an annular member having a key groove 15a on an inner surface thereof and is provided on the inner surface of the hole in the proximal-end surface of the securing member 5a. The second joining portion 152 is a columnar member that has a key 15b capable of passing through the key groove 15a and is secured to the distal-end surface of the ball 9a or the shaft portion 9d. As a result of the second joining portion 152 being inserted into the first joining portion 151 until the key 15b passes beyond the key groove 15a and the second joining portion 152 being subsequently rotated by substantially 90° with respect to the first joining portion 151, the first joining portion 151 and the second joining portion 152 are locked so as not to be moved relative to each other in the longitudinal direction.

With this embodiment, the second device 102B having the treatment tool 2 and the first device 102A having the outer tube 3, the securing portion 4, and the forward-and-backward operating portion 5 are separate components. Therefore, it is possible to exchange the second device 102B with other second device 102B having a treatment tool 2 in a different form. For example, a plurality of second devices 102B that are different in terms of whether the effector 7 is included, the type of the effector 7, bending properties of the bending portion 8, etc. may be prepared and the operator can select a second device 102B to be used from the plurality of second devices 102B.

Other operational effects of this embodiment are the same as those of the first embodiment; therefore, the descriptions thereof will be omitted.

In this embodiment, the first device 102A may be provided as an independent component as the treatment-tool operating device and may be used in combination with an arbitrary treatment tool 2. In this case, instead of the joining portion 151, the first device 102A may include another joining portion that can join the arbitrary treatment tool 2 with the first device 102A and separate the treatment tool 2 therefrom.

It is possible to apply the modifications described in the first embodiment to this embodiment.

Specifically, the securing portion 4 may secure the outer tube 3 to a portion of the endoscope 20 other than the distal-end portion of the insertion portion 21.

The treatment tool 2 may not have the effector 7.

In the case in which the effector 7 has the movable portion 7a, the treatment tool 2 may additionally include the effector operating portion 12, and the effector operating portion 12 may be attached to the forward-and-backward operating portion 5.

The bending operating portion 9 may be secured with respect to an object other than the floor F, such as the hand of the operator, the insertion portion 21, or the operating portion 22.

Figure 12:
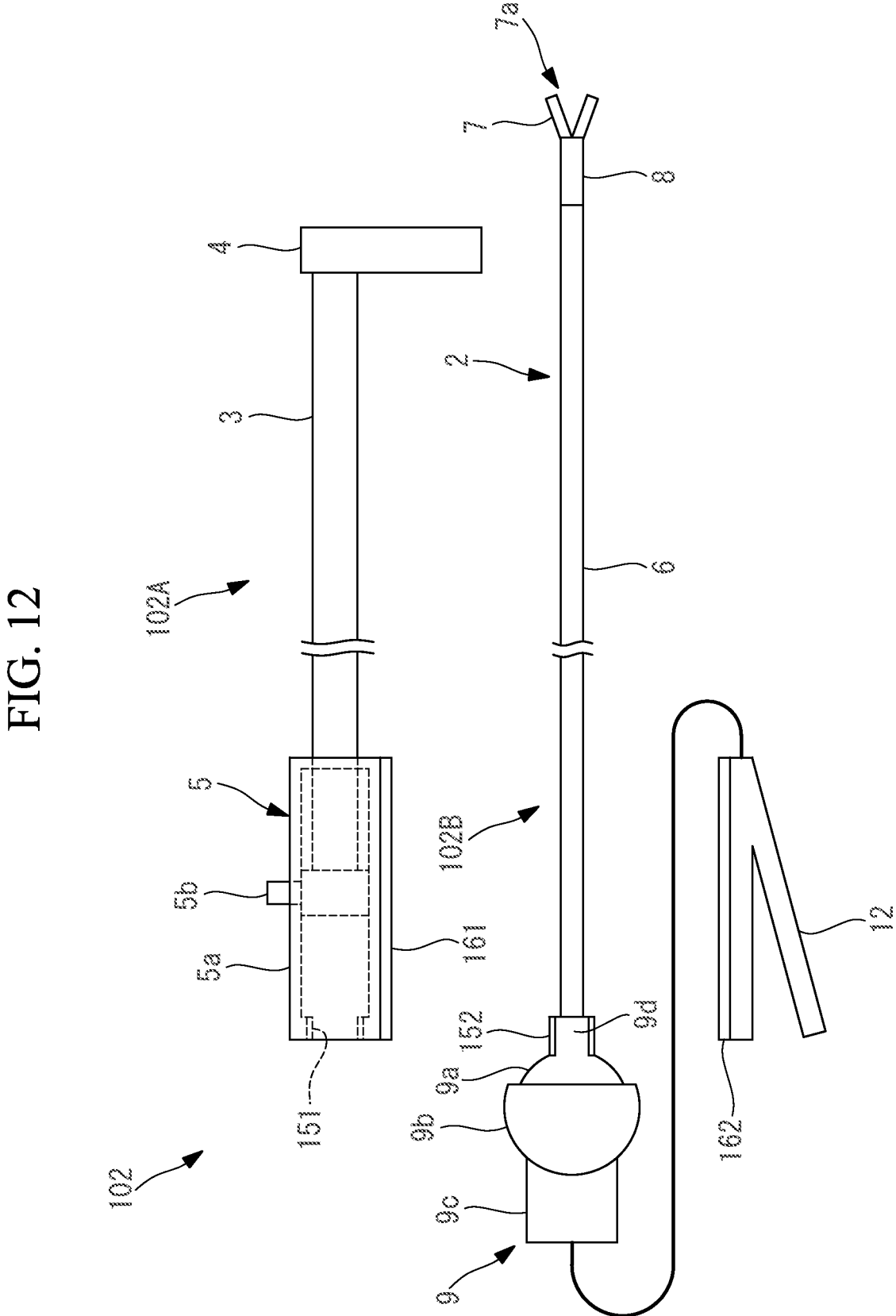
FIG. 12 is an overall configuration diagram of a modification of the treatment device in FIG. 10.

As shown in FIG. 12, in the case in which the treatment tool 2 includes the effector operating portion 12, the treatment device 102 may additionally include joining portions 161 and 162 that join the effector operating portion 12 of the second device 102B with the forward-and-backward operating portion 5 of the first device 102A in a separable manner. The first joining portion 161 is provided in the forward-and-backward operating portion 5, the second joining portion 162 is provided in the effector operating portion 12, and the joining portions 161 and 162 can be joined with and separated from each other.

As a result of integrally assembling the first device 102A and the second device 102B and attaching the effector operating portion 12 to the forward-and-backward operating portion 5 by means of the joining portions 161 and 162, the operator can perform the forward-and-backward operation of the distal end of the treatment tool 2, the bending operation of the bending portion 8, and the operation of the movable portion 7a and use the components by using only one hand.

Figure 13:
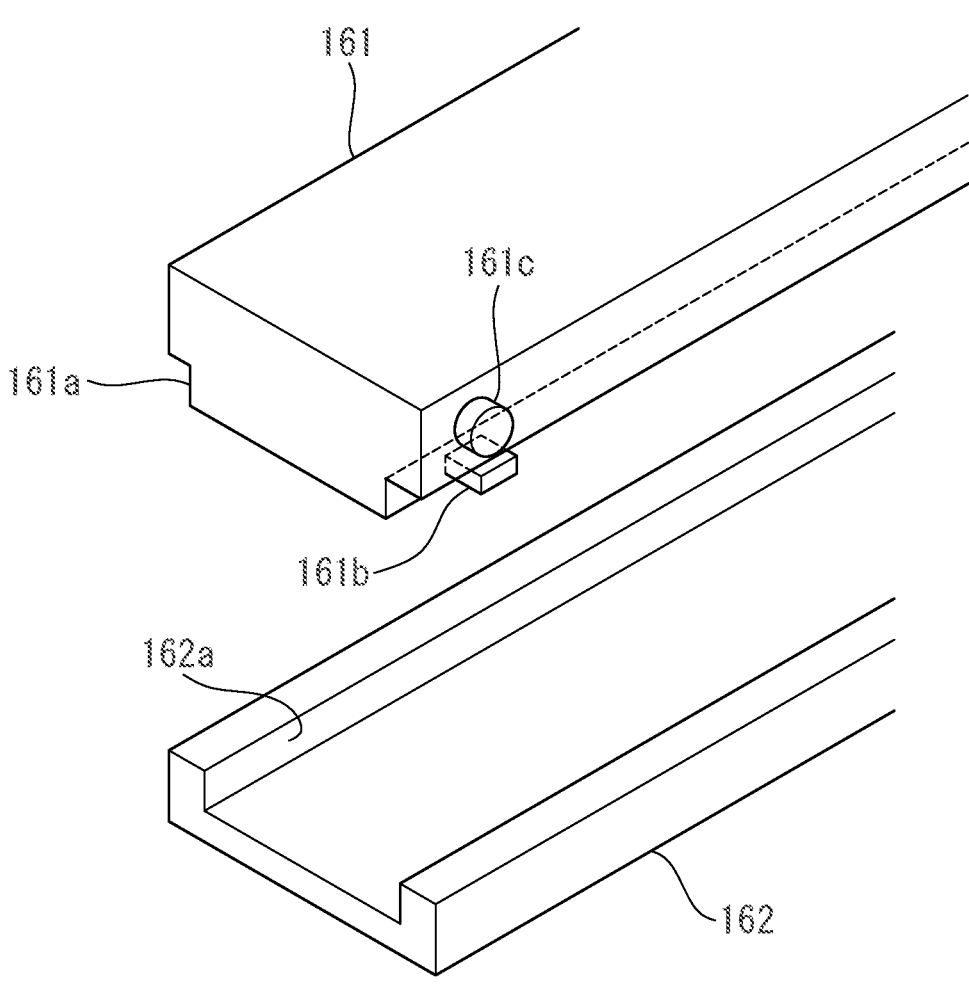
FIG. 13 is a diagram of a configuration example of joining portions that join an effector operating portion to a forward-and-backward operating portion.

FIG. 13 shows a configuration example of the joining portions 161 and 162. The second joining portion 162 has a linear rail 162a and the first joining portion 161 has a slider 161a that can move in the rail 162a. In addition, the slider 161a is provided with a protrusion 161b that is biased in a direction in which the protrusion 161b protrudes from an outer surface of the slider 161*a* by means of an elastic member such as a spring and the rail 162*a* is provided with a depression (not shown) that accepts the protrusion 161*b*.

When the slider 161*a* is inserted into the rail 162*a* and the effector operating portion 12 is slid to a prescribed position with respect to the forward-and-backward operating portion 5, the forward-and-backward operating portion 5 and the effector operating portion 12 are locked so as not to be moved with respect to each other as a result of the protrusion 161*b* fitting into the depression. Accordingly, it is possible to attach the effector operating portion 12 to the forward-and-backward operating portion 5.

The first joining portion 161 is provided with a detachment button 161*c* and the button 161*c* being pressed down causes the protrusion 161*b* to be retracted by resisting the biasing force of the elastic member. Accordingly, as a result of the effector operating portion 12 being slid with respect to the forward-and-backward operating portion 5 while the button 161*c* being pressed down, it is possible to detach the effector operating portion 12 from the forward-and-backward operating portion 5.

Figure 14:
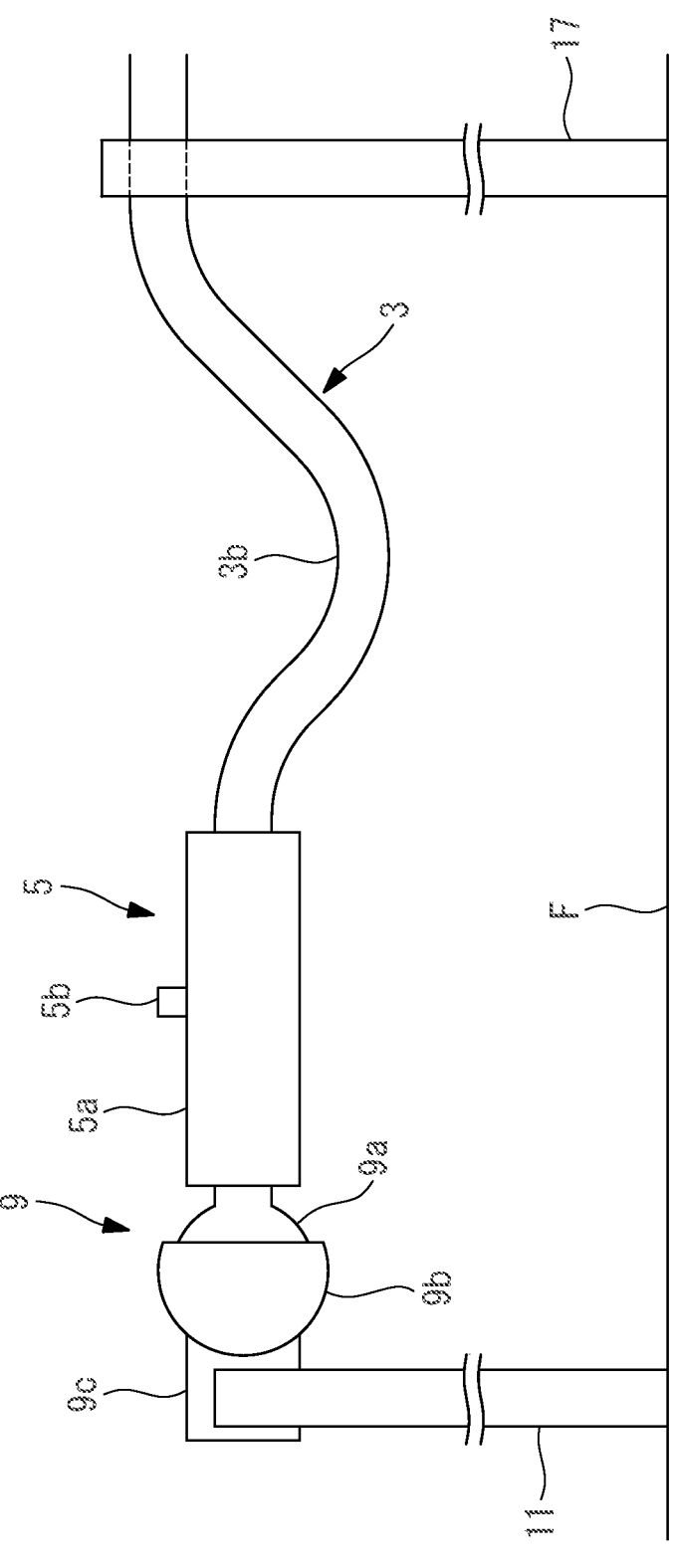
FIG. 14 is a partial configuration diagram of another modification of the treatment system according to the first embodiment of the present invention.

In the above-described first to fourth embodiments, as shown in FIG. 14, the treatment systems 100 and 200 may include another securing member 17 that secures, with respect to the floor F, an intermediate position of the outer tube 3 in the longitudinal direction outside the body.

FIG. 14 shows an example in which the securing member 17 is applied to the treatment system 100 of the first embodiment. In this modification, a portion of the outer tube 3 between the distal end of the forward-and-backward operating portion 5 and the securing member 17 is disposed in a slackened state and forms the slack portion 3*b*.

In the above-described first to fourth embodiments, the bending operating portion 9 is configured so that the ball 9*a* is provided on the distal-end side and the forward-and-backward operating portion 5 is also tilted integrally with the ball 9*a*; however, the configuration of the bending operating portion 9 is not limited thereto and can be altered, as appropriate.

For example, the bending operating portion 9 may have the ball 9*a* on the proximal-end side and the securing member 5*a* of the forward-and-backward operating portion 5 may be secured with respect to the socket 9*b* on the distal-end side. In this case, the posture of the forward-and-backward operating portion 5 is held constant regardless of the inclination of the ball 9*a*.

In the above-described first to fourth embodiments, the movable portion of the outer tube 3 is the proximal-end portion 3*a* of the outer tube 3; however, the movable portion is not limited to the proximal-end portion 3*a* and may be an arbitrary portion of the outer tube 3 disposed on the proximal-end side of the slack portion 3*b*.

As a result of the arbitrary portion disposed on the proximal-end side of the slack portion 3*b* being moved forward and backward, the slack amount of the slack portion 3*b* changes. Therefore, an arbitrary portion other than the proximal-end portion 3*a* can be configured to serve as the movable portion.

In the above-described first to fourth embodiments, the outer tube 3 possesses flexibility over the entire length thereof; alternatively, however, the outer tube 3 may possess flexibility only in a portion thereof in the longitudinal direction and other portions of the outer tube 3 may be rigid. The slack portion 3*b* is formed in a portion possessing flexibility. In this case, it is preferable that a portion of the outer tube 3 disposed outside a body possess flexibility and the slack portion 3*b* be formed outside the body.

The above-described first to fourth embodiments can be carried out in combination, as appropriate.

For example, in the third and fourth embodiments, a forward-and-backward operating portion having the reversing mechanism 14 of the second embodiment may be employed. In addition, in the third embodiment, the joining portions 151 and 152 may be added to the operating portions 5 and 9 and treatment device 101 may be configured so as to be formed from two devices that can be joined with and separated from each other by means of the joining portions 151 and 152.

REFERENCE SIGNS LIST

1, 101, 102 treatment device
2 treatment tool
3 outer tube
3*a* proximal-end portion (movable portion)
3*b* slack portion
4 securing portion
5, 51 forward-and-backward operating portion
5*a* securing member
5*b* operating member
7 effector
11, 17 securing member
12 effector operating portion
14 reversing mechanism
151, 152, 161, 162 joining portion
20 endoscope (guide device)
21*a* bending portion
30 trocar (guide device)
23, 30*a* channel
100, 200 treatment system

The invention claimed is:

1. A treatment device with which a treatment tool is inserted into a body along a longitudinal direction of a long guide device, the treatment device comprising:
   a treatment tool; and
   an outer tube connected to the guide device and into which the treatment tool is inserted, wherein
   the outer tube includes:
   a slack portion formed from a portion of the outer tube in the longitudinal direction of the outer tube, the slack portion being disposed in a slackened state; and
   a movable portion disposed on a proximal-end side of the slack portion, the movable portion being movable forward and backward in the longitudinal direction of the outer tube with respect to the treatment tool in the outer tube, and
   a slack amount of the slack portion changes as a result of the movable portion being moved forward and backward with respect to the treatment tool, and, accordingly, a distal end of the treatment tool disposed farther on a distal-end side than the slack portion is moved in the longitudinal direction of the outer tube.

2. The treatment device according to claim 1, wherein the slack amount of the slack portion is equal to or greater than a prescribed movement amount of the distal end of the treatment tool.

3. The treatment device according to claim 1, wherein:
   the guide device is an endoscope;
   the treatment device further comprises a securing portion configured to secure the outer tube to the endoscope in a detachable manner; and the securing portion is configured to secure the outer tube to the endoscope in parallel thereto on a distal-end side or a proximal-end side of a bending portion of the endoscope.

4. The treatment device according to claim 1, wherein: the guide device is an endoscope or a trocar that has a channel into which the treatment tool is inserted; and the treatment device further comprises a securing portion configured to secure a distal end of the outer tube to an entrance of the channel of the endoscope or the trocar in a detachable manner.

5. The treatment device according to claim 1, further comprising:
a forward-and-backward operating portion that is connected to the movable portion of the outer tube and with which the movable portion is operated in the longitudinal direction of the outer tube.

6. The treatment device according to claim 5, wherein the forward-and-backward operating portion includes:
an operating member configured to be operated by an operator in the longitudinal direction of the outer tube; and
a reversing mechanism comprising a rotation shaft, the reversing mechanism connecting the operating member and the movable portion and moving the movable portion in a direction opposite from a moving direction of the operating member.

7. The treatment device according to claim 5, further comprising:
an effector operating portion attached to the forward-and-backward operating portion and with which an effector of the treatment tool is operated.

8. The treatment device according to claim 5, further comprising:
a first device having the outer tube and the forward-and-backward operating portion;
a second device having the treatment tool; and
one or more joining portions configured to join the first device and the second device with each other in a separable manner.

9. The treatment device according to claim 8, further comprising:
an effector operating portion with which an effector of the treatment tool is operated, wherein the effector operating portion is provided so as to be attached to and detached from the forward-and-backward operating portion.

10. The treatment device according to claim 1, further comprising:
a securing member configured to hold an intermediate position of an extracorporeal portion of the outer tube in the longitudinal direction and secure the intermediate portion with respect to a floor, wherein the slack portion is provided between the movable portion and the securing member.

11. A treatment-tool operating device with which a treatment tool inserted into a body along a longitudinal direction of a long guide device is operated, the treatment-tool operating device comprising:
an outer tube connected to the guide device and into which the treatment tool is inserted, the outer tube including:
a slack portion formed from a portion of the outer tube in a longitudinal direction of the outer tube, the slack portion being disposed in a slackened state; and
a movable portion disposed on a proximal-end side of the slack portion, the movable portion being movable forward and backward in the longitudinal direction of the outer tube with respect to the treatment tool in the outer tube;
a forward-and-backward operating portion connected to the movable portion of the outer tube and with which the movable portion is operated in the longitudinal direction of the outer tube; and
one or more joining portions configured to be joined with the treatment tool in a separable manner.

12. The treatment device according to claim 1, wherein the treatment device is included in a treatment system, the treatment system comprising:
a long guide device to which the outer tube of the treatment device is connected.

13. A treatment-tool operating method for moving a distal end of a treatment tool forward and backward, the method comprising:
connecting an outer tube, into which the treatment tool is inserted, to a long guide device;
forming a slack portion in the outer tube, the slack portion being formed from a portion of the outer tube in a longitudinal direction of the outer tube and disposed in a slackened state; and
moving a movable portion of the outer tube disposed on a proximal-end side of the slack portion in the longitudinal direction of the outer tube with respect to the treatment tool in the outer tube.

14. The treatment device according to claim 6, wherein moving the operating member backward decreases the slack amount of the slack portion to move the distal end forward, and moving the operating member forward increases the slack amount to move the distal end backward.

15. The treatment device according to claim 6, wherein the reversing mechanism is configured such that a forward movement of the operating member results in a forward movement of the distal end, and a backward movement results in a backward movement of the distal end.

16. The treatment device according to claim 1, wherein a movement amount of the distal end is equal to an absolute change of the slack amount of the slack portion between a natural orifice and an operating portion.

* * * * *